(12) United States Patent
Liu et al.

(10) Patent No.: US 12,365,926 B2
(45) Date of Patent: Jul. 22, 2025

(54) SACCHAROMYCES CEREVISIAE STRAIN FOR PRODUCING HUMAN MILK LIPID SUBSTITUTE AND USE THEREOF

(71) Applicants: JIANGNAN UNIVERSITY, Jiangsu (CN); INNER MONGOLIA MENGNIU DAIRY (GROUP) COMPANY LIMITED, Inner Mongolia (CN)

(72) Inventors: Long Liu, Wuxi (CN); Jian Chen, Wuxi (CN); Xueqin Lv, Wuxi (CN); Wenyang Wu, Wuxi (CN); Guocheng Du, Wuxi (CN); Jianghua Li, Wuxi (CN); Guolin Zhou, Wuxi (CN); Yanfeng Liu, Wuxi (CN); Chenyang Zhang, Wuxi (CN)

(73) Assignees: JIANGNAN UNIVERSITY, Jiangsu (CN); INNER MONGOLIA MENGNIU DAIRY (GROUP) COMPANY LIMITED, Inner Mongolia (CN)

( * ) Notice: Subject to any disclaimer, the term of this patent is extended or adjusted under 35 U.S.C. 154(b) by 118 days.

(21) Appl. No.: 18/499,560

(22) Filed: Nov. 1, 2023

(65) Prior Publication Data
US 2024/0067996 A1 Feb. 29, 2024

Related U.S. Application Data

(63) Continuation of application No. PCT/CN2022/143077, filed on Dec. 29, 2022.

(30) Foreign Application Priority Data

Aug. 2, 2022 (CN) .......................... 202210921790.1

(51) Int. Cl.
C12N 15/81 (2006.01)
C12N 9/10 (2006.01)
C12N 9/20 (2006.01)
C12P 7/6409 (2022.01)

(52) U.S. Cl.
CPC .......... *C12P 7/6409* (2013.01); *C12N 9/1029* (2013.01); *C12N 9/20* (2013.01); *C12N 15/81* (2013.01); *C12Y 203/01051* (2013.01); *C12Y 301/01003* (2013.01); *C12N 2800/102* (2013.01)

(58) Field of Classification Search
CPC ........ C12P 7/6409; C12N 15/81; C12N 15/79
See application file for complete search history.

(56) References Cited

U.S. PATENT DOCUMENTS

| 2011/0183387 | A1 | 7/2011 | Nicaud et al. |
| 2013/0149754 | A1 | 6/2013 | Dulermo et al. |
| 2016/0145599 | A1 | 5/2016 | Nicaud et al. |
| 2017/0191073 | A1 | 7/2017 | Brevnova et al. |
| 2024/0067996 | A1* | 2/2024 | Liu ................ C12Y 203/01051 |

FOREIGN PATENT DOCUMENTS

| CN | 108486176 A | 9/2018 |
| CN | 110846293 A | 2/2020 |
| JP | 2007209240 A | 8/2007 |

OTHER PUBLICATIONS

Yeongho Kim et al, "Endoplasmic reticulum acyltransferase with prokaryotic substrate preference contributes to triacylglycerol assembly in Chlamydomonas" PNAS, vol. 115, No. 7, p. 1652-1657 (Feb. 13, 2018).

* cited by examiner

*Primary Examiner* — Tekchand Saidha
(74) *Attorney, Agent, or Firm* — SZDC Law PC

(57) ABSTRACT

The invention provides a *Saccharomyces cerevisiae* strain for producing a human milk lipid substitute. By integrating a heterologous lysophosphatidic acid acyltransferase into *Saccharomyces cerevisiae* and knocking out its own natural lysophosphatidic acid acyltransferase, the content of palmitic acid (C16:0) at Sn-2 position of triacylglycerol produced by *Saccharomyces cerevisiae* is increased, to synthesize a human milk lipid substitute. On this basis, a metabolic pathway related gene is knocked out, to further increase the content of human milk lipid substitute in the product. In the present invention, a human milk lipid substitute is de novo synthesized by *Saccharomyces cerevisiae* for the first time, in which the total fatty acid is 15% or more, and the relative content of C16:0 at Sn-2 position reaches about 60%.

9 Claims, 3 Drawing Sheets

Specification includes a Sequence Listing.

A: heterologous gene is directly integrated into the genome

B: knock out the signal peptide of heterologous gene itself

C: introduce endoplasmic reticulum to localize the signal peptide

SACCHAROMYCES CEREVISIAE STRAIN FOR PRODUCING HUMAN MILK LIPID SUBSTITUTE AND USE THEREOF

This application is a Continuation application of PCT/CN2022/143077, filed on Dec. 29, 2022, which claims priority to Chinese Patent Application No. CN 202210921790.1, filed on Aug. 2, 2022, which is incorporated by reference for all purposes as if fully set forth herein.

A Sequence Listing XML file named "10015_0136.xml" created on Nov. 1, 2023, and having a size of 91,425 bytes, is filed concurrently with the specification. The sequence listing contained in the XML file is part of the specification and is herein incorporated by reference in its entirety.

FIELD OF THE INVENTION

The invention relates to the field of biological technology, and more particularly to a *Saccharomyces cerevisiae* strain for producing human milk lipid substitute and use thereof.

DESCRIPTION OF THE RELATED ART

Infants are populations in a special growth stage. In this stage, they need a lot of comprehensive nutrients, and the quantity and quality of nutrient intake in this stage directly affect the future growth and development of infants. Human milk is the most direct source of energy and nutrients for infants, which contains a large number of special ingredients that can promote the healthy growth and development of infants.

Human milk lipid is the main nutrient in human milk, accounting for 3%-5% of human milk. 98% of the human milk lipid is triacylglycerols, which are the main energy source for infant growth and development. At the age of 0-6 months, the human milk lipid provides 40%-50% of the energy needed for infants, and the human milk lipid also provides essential fatty acids for infants. Studies show that both the fatty acid composition and the distribution position of fatty acids in human milk lipids are key factors determining whether infants can absorb nutrients in human milk. Nearly 50% of the fatty acids at position 2 (Sn-2) of human milk lipid is palmitic acid. This particular triacylglycerols structure enables infants to better absorb calcium ions, which can effectively prevent diarrhea, avoid infant malnutrition, and reduce infant mortality. However, although human feeding is the best way to feed infants, there are situations where human feeding cannot be used for some reasons. In such cases, infant formula suitable for infants, with human milk as the gold standard, becomes an ideal product to replace human milk.

In recent years, researchers in China and other countries not only focused on the composition and contents of fatty acids in human milk, but also paid more attention to the location distribution of fatty acids in triacylglycerol of human milk. In human milk lipids, palmitic acid (16:0) is esterified to the middle (Sn-2 or 3) position in the main chain of glycerol, and oleic acid (18:1) is mainly esterified to the outer (Sn-1,3) position, such that triacylglycerols (TGs) has a unique stereoisomeric structure promoting the absorption of nutrients in infants' intestines. However, most of the lipid used in infant formula milk powder is derived from animals. Different from the structure of triacylglycerol in human milk, unsaturated fatty acids such as C18:1 in animal-derived triacylglycerol are mainly located at the middle (Sn-2 or 3) position in the main chain of glycerol, and saturated fatty acids such as C16:0 are mainly located at the outer (Sn-1,3) position in the main chain of glycerol, which is not conducive to the absorption and growth of infants.

At present, the human milk lipid substitute (triacylglycerol with the particular structure) is mainly enzymatically synthesized, which occupies a dominating position in the market. For example, camellia seed oil is used as a raw material, and palmitic acid is used as an acyl donor to enzymatically synthesize triacylglycerol rich in palmitic acid at Sn-2 position in an organic solvent system by Xiong Zhiqin (Enzymatic Preparation and Property Study of Human Milk Lipid Substitute). With the production and development of human milk lipid substitutes, biological de novo synthesis has attracted more and more attention because of its easy control and ability to synthesize various desired products. Industrial production of strains through genetic engineering to produce specific lipid compositions has great potential. Meanwhile, genetic engineering methods are used to construct de novo synthetic products from genetically engineered strains, which have many advantages such as low cost, unrestricted raw materials, simple extraction process, no seasonality, short production time, and low environmental pollution, so it is favored by scholars. For example, an *Arabidopsis* plant that can synthesize human milk substitutes constructed by genetic engineering in *Arabidopsis thaliana*. Human milk substitute is also synthesized in microorganisms by researchers by changing the substrate supply. However, there is no report on the preparation of a human milk lipid substitute by de novo synthesis.

SUMMARY OF THE INVENTION

To solve the above problems, the present invention provides an engineered *Saccharomyces cerevisiae* strain for synthesizing a human milk lipid substitute. The human milk lipid substitute is synthesized by integrating a heterologous lysophosphatidic acid acyltransferase into *Saccharomyces cerevisiae* and knocking out its natural lysophosphatidic acid acyltransferase, the content of palmitic acid (16:0) at Sn-2 position of triacylglycerol produced by *Saccharomyces cerevisiae* is increased. On this basis, a metabolic pathway-related gene is knocked out, to further increase the content of human milk lipid substitute in the product.

The first object of the present invention is to provide a recombinant *Saccharomyces cerevisiae* strain for producing a human milk lipid substitute. In the recombinant *Saccharomyces cerevisiae* strain, a lysophosphatidic acid acyltransferase CrlPAAT1 is expressed, SLC1, ALE1, and LOA1 genes encoding lysophosphatidic acid acyltransferase are knocked out, and TGL3, TGL4 and TGL5 genes encoding triglyceride lipase are knocked out.

In the lysophosphatidic acid acyltransferase CrlPAAT1, the self-localization signal peptide is knocked out, and an endoplasmic reticulum localization signal peptide is linked to the C terminal.

Preferably, the lysophosphatidic acid acyltransferase CrlPAAT1 has a nucleotide sequence as shown in SEQ ID NO: 4. Specifically, the sequence is as follows:

CAAAAAAGATCTCAAAACAGAAGAACCAACCCAAGCAGCCAAAACCAAAG

CAACAACTTGTTGAGCAGCACCAGTAGCAGCCAAAGCTGCAGCCAAACCT

CTCCAAGAACCATAACAAACACCAGCAAAAACCAAAATAGAAACCAAAGT

AATAGCCAATTGTTGAACCCACATAGATGAAGAATAAGAATAAGCTTGTG

-continued

```
GACCAGGCATAGAAAATCTTGGAACATTTTTCAAATCTTCCAAACCATAA

GTAGCAGCCCAACAAGAATCCCAAGTAGCTTGCAAATCAGTAAAAAAGC

TTCAAAATTTGGATAATCAGCAGATTTCAAAACCTTAGAAAAAGTAGTAA

CACAAGTTCTACCAAAATGAACAGATTGAGATTTTTCAGACAAAACTTCA

TCTTTACCTCTAGTAACAACAATTTGAACAGGCAATTTTCTAGAATGAGC

ATAATGCAACATACCTCTTTTCAATGGCAAAGAAGCAGGTTTAGTAGATC

TATGACCTTCAGGATAAACCAACAAACCAGGAACATGAGAAGAACCCAAA

GTTTGATCCAACCAAGCATTAAAAGCTTCTTTATCAGCAATAGTACCTCT

CTTAAACAAAACAATACCTTTCAAAATCATGCAAGAAGTACAAAAAACAG

GGAAAACAAAATAAACCAACCATCTAGACATTAAAGCAGCTCTACCTTCA

GTCAAATAAGCATCAATAAAAAAATCAGCCCAAGATCTATGATTACACAA

ATACAAACATGGACCACCTTTATACAAAGTATGTTCACCAGCTTGCAACA

AAGTAACTCTAAAATAAGCAACCAAAGCTCTAGCCCAATCCAACATATCA

TTTCTTTTACCCAAAGAAGCGAATCTGATTCTATATAAAATAGCAAAGAT

TGGTAAAGACCAATAAAAAACAAAAACAGAAAACAAGAAAGATGGTAAAC

CCAACCATTTAGTCAAAACAGACAT.
```

Preferably, the self-localization signal peptide of the lysophosphatidic acid acyltransferase CrlPAAT1 has a nucleotide sequence as shown in SEQ ID NO: 8.

Specifically, the sequence is as follows:

```
TTGATCCAACCAAGCATTAAAAGCTTCTTTATCAGCAATAGTACCTCTCT

TAAACAAAACAATACCTTTCAAAATCATGCAAGAAGTACAAAAAACAGGG

AAAACAAAATAAACCAACCATCTAGACATTAAAGCAGCTCTACCTTCAGT

CAAATAAGCATCAATAAAAAAATCAGCCCAAGATCTATGATTACACAAAT

ACAAACATGGACCACCTTTATACAAAGTATGTTCACCAGCTTGCAACAAA

GTAACTCTAAAATAAGCAACCAAAGCTCTAGCCCAATCCAACATATCATT

TCTTTTACCCAAAGAAGCGAATCTGATTCTATATAAAATAGCAAAGATTG

GTAAAGACCAATAAAAAACAAAAACAGAAAACAAGAAAGATGGTAAACCC

AACCATTTAGTCAAAACAGA.
```

Preferably, the endoplasmic reticulum localization signal peptide is HDEL, the nucleotide sequence as shown in SEQ ID NO: 13. The endoplasmic reticulum localization signal peptide is expressed in the heterologous lysophosphatidic acid acyltransferase, to modify the heterologous acyltransferase, such that the heterologous acyltransferase can be retained in the endoplasmic reticulum to exert its function. Specifically, the sequence is as follows:

```
TCAGAACAAGCAGCACAACAAGCAGTTAATAATGCGGGCTGGTCAGTTAT

TTCAGCAGCACAACTGGGCTATGCGGGCAAAACAGATGCAAGAGGCACAT

ATTATGGCGAAACAGCGGGCTATACAACAGCACAAGCAGAAGTTCTGGGC

AAATATGATTCAGAAGGCAATCTGACAGCAATTGGCATTTCATTTAGAGG

CACAAGCGGCCCGAGAGAATCACTGATTGGCGATACAATTGGCGATGTTA

TTAATGATCTGCTGGCGGGCTTCGGCCCGAAAGGCTATGCAGATGGCTAT
```

-continued

```
ACACTGAAAGCATTTGGCCAACTGCTGGGCGATGTTGCAAAATTTGCACA

AGCACATGGCCTGAGCGGCGAAGATGTTGTGGTTAGCGGCCAT.
```

Preferably, plasmid pMHyLp-LEU is used as an expression vector for the gene expressing the lysophosphatidic acid acyltransferase CrlPAAT1, and pMHyLp-LEU has a nucleotide sequence as shown in SEQ ID NO: 5.

Preferably, SLC1 has a nucleotide sequence as shown in SEQ ID NO: 15, ALE1 has a nucleotide sequence as shown in SEQ ID NO: 16, and LOA1 has a nucleotide sequence as shown in SEQ ID NO: 17.

Preferably, TGL3 has a nucleotide sequence as shown in SEQ ID NO: 18, TGL4 has a nucleotide sequence as shown in SEQ ID NO: 19, and TGL5 has a nucleotide sequence as shown in SEQ ID NO: 20.

Preferably, the recombinant *Saccharomyces cerevisiae* strain is constructed with *S. cerevisiae* CEN PK2-1C, W303, FY1679, or BY4743 as a starting strain.

In the invention, the recombinant *Saccharomyces cerevisiae* strain is constructed through a method comprising the following steps in an arbitrary order:

S1: knock out the self-localization signal peptide of the lysophosphatidic acid acyltransferase coding gene, and connect the endoplasmic reticulum localization signal peptide at the C terminus to obtain the lysophosphatidic acid acyltransferase gene. Introducing the lysophosphatidic acid acyltransferase gene into *Saccharomyces cerevisiae*;

S2: knock out the own lysophosphatidic acid acyltransferase coding genes (SLC1, ALE1 and LOA1) of *Saccharomyces cerevisiae*;

S3: knock out the own triglyceride lipase coding genes (TGL3, TGL4, and TGL5) of *Saccharomyces cerevisiae*, to obtain the recombinant *Saccharomyces cerevisiae* strain.

Preferably, in Step S1, the lysophosphatidic acid acyltransferase coding gene is integrated into the genome of *Saccharomyces cerevisiae* by Cre/loxp technology, through a process comprising the following steps:

1) integrating and expressing the lysophosphatidic acid acyltransferase coding gene by the Cre/loxp system as shown in SEQ ID NO: 5, SEQ ID NO: 6, and SEQ ID NO:7, using constitutive promoters $P_{TEF1}$, $P_{TDH1}$, $P_{PGK1}$, $P_{PYK}$, $P_{INO2}$, $P_{ITR1}$, $P_{ALD5}$, $P_{ION1}$, $P_{LEU2}$, and $P_{ZWF1}$, and terminators $T_{ADH1}$, $T_{DNM1}$, $T_{TPS1}$, $T_{TDH3}$, $T_{SLX5}$, $T_{ATP5}$, and $T_{CYC1}$, and designing PCR primers so that the overlapping region of adjacent fragments of the gene expression frame reaches 40 to 100 bp, to construct a gene expression and integration frame of CrlPAAT1 (NCBI Reference Sequence: XP_042921325.1);

2) integrating the expression frame of the lysophosphatidic acid acyltransferase coding gene to the site 104c, 416d, 208c, 1622a, 308a, and 911b of *Saccharomyces cerevisiae* by the Cre/loxp method.

Preferably, in Step S2, the own lysophosphatidic acid acyltransferase coding genes ALE1, LOA1, and SLC1 of *Saccharomyces cerevisiae* are knocked out by the Cre/loxp method.

A second object of the present invention is to provide the use of the above-mentioned *Saccharomyces cerevisiae* strain in the preparation of human milk lipid substitute.

Preferably, the use includes the step of fermenting and producing human milk lipid substitutes by using glucose as a substrate.

Preferably, in the fermentation and production process, the pH is 6.0-8.0.

Preferably, in the fermentation and production process, the temperature is 20-30° C.

Preferably, the *Saccharomyces cerevisiae* strain is inoculated into a sterile medium with no amino nitrogen source, a YPD sterile medium with limited nitrogen source, an inorganic salt sterile medium, or a soybean peptone sterile medium with limited nitrogen source where glucose is used as a carbon source, and fermented with ventilation at pH 6.0-8.0, 200-300 rpm, and 20-30° C.

The present invention has the following beneficial effects.

With the recombinant *Saccharomyces cerevisiae* provided in the present invention, a human milk lipid substitute can be produced by fermentation in a sterile medium having glucose as a carbon source, which lays a foundation for the metabolic engineering of *Saccharomyces cerevisiae* to synthesize a human milk lipid substitute. The construction method for recombinant *Saccharomyces cerevisiae* provided in the present invention is simple and convenient and has a good application prospect.

DETAILED DESCRIPTION OF THE PREFERRED EMBODIMENTS

Figure 1:
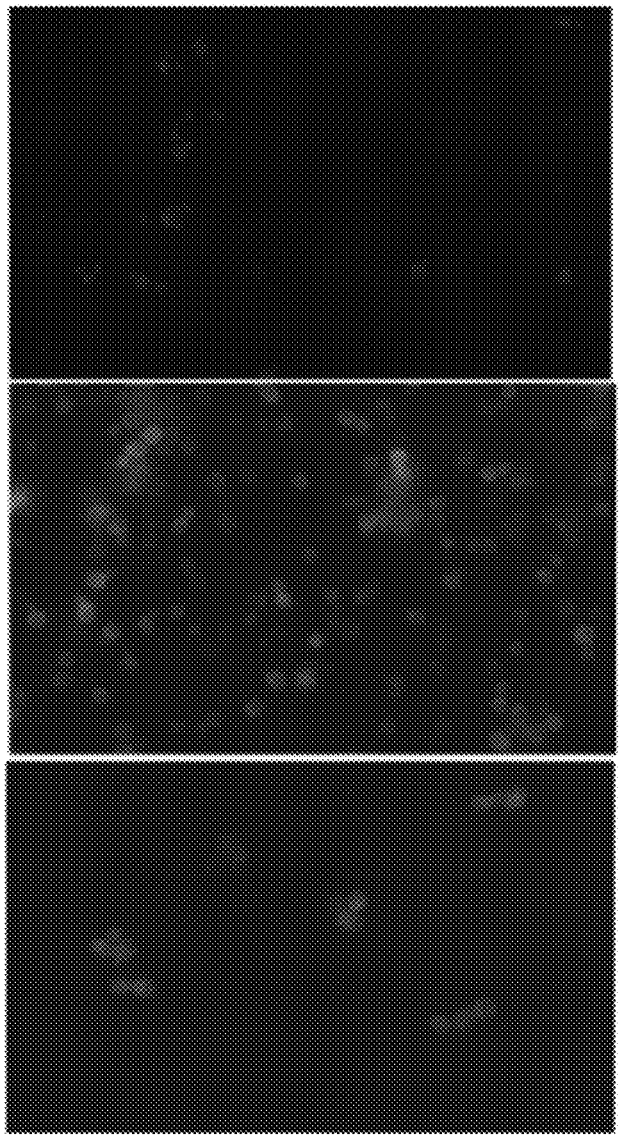
FIG. 1 Change in localization of the heterologous gene CrlPAAT1.

The present invention will be further described below with reference to the accompanying drawings and specific examples, so that those skilled in the art can better understand and implement the present invention; however, the present invention is not limited thereto.

Experimental Materials Involved:
250 ml shake flask, two-pan/single-pan analytical balance, Electric Sterilizer, recombinant strain, shaking table Culture Medium (g/L):
YNB medium: YNB 3.4, ammonium sulfate 10, glucose 20, uracil 0.05, histidine 0.05, leucine 0.05 and tryptophan 0.05;

YPD sterile medium with limited nitrogen source: glucose 20, yeast extract 10, and peptone 10;

Inorganic salt sterile medium: glucose 10, $(NH_4)_2SO_4$ 1, $K_2HPO_4$ 0.125, $KHPO_4$ 0.875, KI 0.0001, $MgSO_4 \cdot 7H_2O$ 0.5, $CaCl_2 \cdot 2H_2O$ 0.1, NaCl 0.1, stock solution of trace elements 1 mL, and stock solution of vitamins 1 mL;

Basal fermentation medium with limited nitrogen source: glucose 20, ammonium sulfate 4, $KH_2PO_4$ 2.5, and $MgSO_4 \cdot 7H_2O$ 0.5.

Seed medium: YNB medium, inorganic salt sterile medium, YPD sterile medium with a limited nitrogen source, basal fermentation medium with a limited nitrogen source.

Fermentation medium: YNB medium, inorganic salt sterile medium, YPD sterile medium with a limited nitrogen source, and basal fermentation medium with a limited nitrogen source.

Detection Methods Involved:
Gas chromatography-mass spectrometry (GC-MS): Shimadzu (GCMS-QP2010 SE), SH-Rtx-Wax column, mobile phase He, column temperature 100° C., injection volume 1 μL, split ratio 20:1, flow rate 1.0 ml/min.

In the present invention, recombinant *S. cerevisiae* CEN PK2-1C MATa; ura3-52; trp1-289; leu2-3,112; his3-Δ1; MAL2-8C; SUC2; *S. cerevisiae* W303 MATa; ura3-1; trp1-Δ1; leu2-3,112; his3-11; ade2-1; can1-100; *S. cerevisiae* FY1679MATa; ura3-52; trp1-Δ63; leu2-Δ1; his3-Δ200; GAL2 and *S. cerevisiae* BY4743 MATa; ura3-Δ0; met15-Δ0; leu2-Δ0; his3-Δ1; and lys-Δ0 are used as a starting strain, the lysophosphatidic acid acyltransferase coding gene derived from Chlamyolomonas is integrated into the genome of *Saccharomyces cerevisiae* by the Cre/loxp method, thereby obtaining a *Saccharomyces cerevisiae* strain capable of synthesizing a human milk lipid substitute (triacylglycerol).

*Saccharomyces cerevisiae* is also called baker's yeast or brewer's yeast. *Saccharomyces cerevisiae* is a yeast species most extensively related to human beings. As a safety strain for food, it has been used in making bread, steamed bread, other foods, and in the wine industry. In recent years, the scholars study the use of *Saccharomyces cerevisiae* to produce natural products, such as artemisinin and *Panax notoginseng* saponins. *Saccharomyces cerevisiae* has the advantages of high safety, low pathogenicity, high stress resistance and low probability of being contaminated by phage, so it also plays an important role in the field of genetic engineering. However, the triacylglycerol structure in *Saccharomyces cerevisiae* is quite different from that in human milk. Therefore, in order to obtain an engineering strain for the production of human milk lipid substitutes, the Cre/loxp technology is used to integrate an acyltransferase metabolic pathway into *Saccharomyces cerevisiae*, so as to achieve the effect of producing human milk lipid substitute.

Primers used in the following examples are shown in the table below:

| | | |
|---|---|---|
| F1 | AGTATTATCTCTGCTGGTCGGTACTTAAATTGG | |
| | (SEQ ID NO: 22) | |
| R1 | AAAAAATCGGATGTTGAATGGGCATAAATATAAATGTATATATAAgctattacgccagctg | |
| | (SEQ ID NO: 23) | |
| F2 | TCATGACATTGACGAGAGTTTCTCTCGTACCCATATT | |
| | (SEQ ID NO: 24) | |
| R2 | TCAGGGGTAATTAACTTGTTAACTTTGGAGAAGTAAATGAAAAATG | |
| | (SEQ ID NO: 25) | |
| F3 | GAAAGATGGTAAACCCAACCATTTAGTCAAAACAGACATatagcttcaaaatgtttctactcctttt | |
| | (SEQ ID NO: 26) | |

-continued

R3  CGAATACCTCAGAACATCATCTTTTCAGCAAGtagttctagaaaacttagattagattgct
    (SEQ ID NO: 27)

F4  CATAAATATAAATGTATATATAAgctattacgccagctgaattggagcgacctcatgctatactgagaaagca
    (SEQ ID NO: 28)

R4  CGAAGATGTTGTGGTTAGCGGCCATaattcttcgccagaggtttggtcaagtctc
    (SEQ ID NO: 29)

F5  TGCTTGTTGTGCTGCTTGTTCTGACAAAAAAGATCTCAAAACAGAAGA
    (SEQ ID NO: 30)

R5  aaaggagtagaaacattttgaagctatATGTCTGTTTTGACTAAATGGTTGGGTTTACCATCTTTCTT
    (SEQ ID NO: 31)

F6  gcaatctaatctaagttttctagaactaCTTGCTGAAAAGATGATGTTCTGAGGTATTCG
    (SEQ ID NO: 32)

R6  TGTTTTGTATGCTATTTCATTTTTCATTTACTTCTCCAAAGTTAACAAGTTAATTACCCCTGAAGCCGCCTTGC
    (SEQ ID NO: 33)

F7  AACCAACAAACCAGGAACATGAGAAGAACCCAAAGTCATatagcttcaaaatgtttctactcctttt
    (SEQ ID NO: 34)

R7  aaaggagtagaaacattttgaagctatATGACTTTGGGTTCTTCTCATGTTCCTGGTTTGTTGGTT
    (SEQ ID NO: 35)

F8  ttgaccaaacctctggcgaagaattATGGCCGCTAACCACAACATCTTCGCCGC
    (SEQ ID NO: 36)

R8  TCTTCTGTTTTGAGATCTTTTTTGTCAGAACAAGCAGCACAACAAGCAGTT
    (SEQ ID NO: 37)

F9  AAACCAGGAACATGAGAAGAACCCAAAGTATGGCCGCTAACCACAACATCTTCGCCGCT
    (SEQ ID NO: 38)

R9  aaaggagtagaaacattttgaagctatATGTCAGAACAAGCAGCACAACAAGCAGTTAATAATGC
    (SEQ ID NO: 39)

F10 TTACCTTCATATGACAAAATTTCGTTGGACTCATCGTC
    (SEQ ID NO: 40)

R10 TACCTCAGAACATCATCTTTTCAGCAAGTATTTTTTTGCTCGAATTCACTGACGGAGGGA
    (SEQ ID NO: 41)

F11 GCTTCAGGGGTAATTAACTTGTTAACTTCACATTTTTAGAGTAGTATATA
    (SEQ ID NO: 42)

R11 CTTTAGCAATATCGGACAAACAGCCGTATTTTTTATTCT
    (SEQ ID NO: 43)

F12 CTATCTTGGGGGTACGAAACTTAGCAATATATTTAGCAA
    (SEQ ID NO: 44)

R12 TGGACCAGAACTACCTGTGAAATTAATGTTGGAAGCGATCAGCAGCAGAAT
    (SEQ ID NO: 45)

F13 CTAACAAAATAGCAAATTTCGTCAAAAAATGGCCAAAAACGACAGATG
    (SEQ ID NO: 46)

R13 GTGAAGACAAATTATCTAAGGTCCAACTCTACGAAGATTT
    (SEQ ID NO: 47)

F14 ATAGACGTTTCTAAACCCAAATGAATCCAAGTTGCCGA
    (SEQ ID NO: 48)

F15 TCAATGACGAGGTTCTCACCCCTGCCCAGGTATCTTGTATTTTGTCACCTCGTAGGAGCTACTT
    (SEQ ID NO: 49)

R14 TCCTAGCGCTCACCAAGCTCTgAAATACTTATGAAGGCATGCATG
    (SEQ ID NO: 50)

R15 AGGATCATTCTGGTAATACCCCATTTAAAATACCTCATCGAA
    (SEQ ID NO: 51)

F16 GTTTCCCTCCGTCAGTGAATTCGAGCAAAAAAATACTTGCTGAAAAGATGATGTTCTGAGGTA
    (SEQ ID NO: 52)

R16 TATATACTACTCTAAAAATGTGAAGTTAACAAGTTAATTACCCCTGAAGC
    (SEQ ID NO: 53)

-continued

F17 TTCTGCTGCTGATCGCTTCCAACATTAATTTCACAGGTAGTTCTGGTCCAT
(SEQ ID NO: 54)

R17 ATCTGTCGTTTTTGGCCATTTTTTGACGAAATTTGCTATTTTGTTA
(SEQ ID NO: 55)

F18 CATGCATGCCTTCATAAGTATTTcAGAGCTTGGTGAGCGCTAGGAGTC
(SEQ ID NO: 56)

R18 CTACGAGGTGACAAAATACAAGATACCTGGGCAGGGGTGAGAACCTCGTCATTGA
(SEQ ID NO: 57)

F19 ATAGCCTCGACGCCAGCTTTGATTAGTTCATCCGGGTTCCCG
(SEQ ID NO: 58)

F20 CTTCAGGGGTAATTAACTTGTTAACTTTATCGTTTCCACTTTTTTCTGTCTTATTTTTTTATTGATAG
(SEQ ID NO: 59)

F25 ACATCTTTGAGTTGCCGTTAAGCCTTGCTGAAAAGATGATGTTCTGAGGTATTCGTATCGCTAGCTTGATAC
(SEQ ID NO: 60)

R19 ATACCTCAGAACATCATCTTTTCAGCAAGGCTTAACGGCAACTCAAAGATGTGA
(SEQ ID NO: 61)

R20 TTGGTCCTATTCAGCGACCAATCAGTGCTTCCTGCCCACTTT
(SEQ ID NO: 62)

R25 AAAAGTGGAAACGATAAAGTTAACAAGTTAATTACCCCTGAAGCCGCCTTGCATG
(SEQ ID NO: 63)

F21 GGGATCCTCTTGCGAAGCACGCTCGCTGGGCCTGGAA
(SEQ ID NO: 64)

F22 ACAAAATAGCAAATTTCGTCAAAAAGAAAACACGGGCTTGCTTATATATCCTCTAGATATTCTT
(SEQ ID NO: 65)

F26 GAGTACAGGTATATGTAATAAAAGTCTGAATTAATTTCACAGGTAGTTCTGGTCCATTGGTGAAAGTTTGCGGCTTG
(SEQ ID NO: 66)

R21 GAACTACCTGTGAAATTAATTCAGACTTTTATTACATATACCTGTACTCCCTTCAATAATTA
(SEQ ID NO: 67)

R22 GTTATTATGTTGGCAATGGAAAAGTTGCGTACCGAGATACCGTAA
(SEQ ID NO: 68)

R26 ATATAAGCAAGCCCGTGTTTTCTTTTTGACGAAATTTGCTATTTTGTTAGAGTCTTTTACAC
(SEQ ID NO: 69)

F23 TGCTGGAGCAAGCTCCGTCTCCAGCTCGGGAAGTGT
(SEQ ID NO: 70)

F24 CGAGGTTCTCACCCCTGCCCAGGTATTGAACAATTCAGACATTTTTCAAAATTGAAATGAAAGACA
(SEQ ID NO: 71)

F27 ACAAGGAAGACGGTTCTGTTTCGTTGCTAGAGCTTGGTGAGCGCTAGGAGTCACTGCCAGGTATCGTTT
(SEQ ID NO: 72)

R23 CCTAGCGCTCACCAAGCTCTAGCAACGAAACAGAACCGTCTTCCTTGTGCTGTTTATGATG
(SEQ ID NO: 73)

R24 ATTTCCTATGAATAATCAAGACATAATGAATTTTCAATGGCTATTGAACTTCCC
(SEQ ID NO: 74)

R27 AATTTTGAAAAATGTCTGAATTGTTCAATACCTGGGCAGGGGTGAGAACCTCGTCATTGATGGACAGGT
(SEQ ID NO: 75)

Example 1. Construction of *Saccharomyces cerevisiae* Strain (TG-1 to TG-4) Expressing Heterologous Acyltransferase Based on the lysophosphatidic acid acyltransferase Crl-PAAT1 (NCBI Reference Sequence: XP_042921325.1) derived from Chlamyolomonas publicized on NCBI, codon optimization was carried out according to the codon preference of *Saccharomyces cerevisiae*, and whole gene was synthesized. According to the design method of primers for overlap extension PCR, primers were designed to make the overlapping region of adjacent fragments of a gene expression frame reach 40-100 bp. Primers were designed to amplify the upstream and downstream homologous arms of the site 911b on the chromosome of *Saccharomyces cerevisiae* CEN PK2-1C, the promoters $P_{TEF1}$, $P_{TDH1}$, $P_{PGK1}$, $P_{PYK}$, $P_{INO2}$, $P_{ITR1}$, $P_{ALD5}$, $P_{ION1}$, $P_{LEU2}$ and $P_{ZWF1}$, the terminators $T_{ADH1}$, $T_{DNM1}$, $T_{TPS1}$, $T_{TDH3}$, $T_{SLX5}$, $T_{ATP5}$ and $T_{CYC1}$, and the signal peptide (HDEL) fragment.

Using the whole-gene synthesized CrlPAAT1 plasmid as a template, primers were designed to amplify heterologous lysophosphatidic acid acyltransferase. Using the plasmid pMHyLp-LEU as a template (as shown in SEQ ID NO:5), a defective tag fragment was obtained by PCR amplification, and a gene integration frame was obtained by overlap extension PCR.

(1) Using the primers F1 and R1, and F2 and R2, the upstream and downstream homologous arm fragments of the site 911b were amplified; using the primers F3 and R3, the promoter $P_{TEF1}$ fragment was obtained by amplification; using the primers F4 and R4, the terminator $T_{ADH1}$ fragment was obtained by amplification; using the primers F5 and R5, the CrlPAAT1 gene fragment as shown in SEQ ID NO: 4 was obtained by amplification; and the pMHyLp-LEU fragment was amplified using the primers F6 and R6. A gene expression frame was constructed by overlap extension PCR and transferred into Saccharomyces cerevisiae CEN PK2-1C, to obtain the strain TG-1.

(2) Using F5 and R7, the self-localization signal peptide (as shown in SEQ ID NO: 8) of the CrlPAAT1 gene (having a gene sequence as shown in SEQ ID NO: 4) was knocked out, to obtain the mCrlPAAT1 gene. A gene expression frame constructed with the homologous arms in (1), the (F7 and R3) promoter, the terminator, and the defective tag fragment following the process in (1) was transferred into Saccharomyces cerevisiae CEN PK2-1C, to obtain the strain TG-2.

(3) Using the primers F8 and R8, and F9 and R9, the fragments of signal peptide HDEL (as shown in SEQ ID NO: 13) connected to the C and N terminals of mCrlPAAT1 gene were obtained by amplification. A gene expression frame constructed by the fragment of signal peptide HDEL connected to the C terminal of mCrlPAAT1 gene and the fragment of mCrlPAAT1 gene in (2) was transferred to Saccharomyces cerevisiae CEN PK2-1C to obtain the strain TG-3. A gene expression frame constructed by the fragment of signal peptide HDEL connected to the N terminal of mCrl-PAAT1 gene and the fragment of mCrlPAAT1 gene in (2) was transferred to Saccharomyces cerevisiae CEN PK2-1C to obtain the strain TG-4.

The strains TG-3 and TG-4 were detected, and it was found that the relative content of C16:0 at the Sn-2 position of TAG in strain TG-3 was increased to 40%, so the strain TG-3 was used for subsequent experiments. In the above process, the constructed gene integration frame was transformed into competent cells of Saccharomyces cerevisiae by lithium acetate transformation. Colonies were picked up for PCR verification and some transformants verified to be correct by PCR were used for sequencing verification.

Example 2. Construction of Saccharomyces cerevisiae Strain (TG-5-TG-14) Highly Producing Human Milk Lipid Substitute According to the design method of primers for overlap extension PCR, using the genome of Saccharomyces cerevisiae CEN PK2-1C as a template, the upstream and downstream homologous arms of SLC1 (F10, R10 and F11, R11), ALE1 (F12, R12 and F13, R13) and LOA1 gene (F14, R14 and F15, R15) were obtained by amplification. Using the plasmid pMHyLp-LEU (F16, R16), pMHyLp-HIS (F17, R17) and pMHyLp-TRP (F18, R18) as a template (as shown in SEQ ID NO: 5 to SEQ ID NO: 7), to obtain defective expression frame fragments by amplification. A gene integration frame was obtained by overlap extension PCR. On the basis of strain TG-3, single knockout, double knockout and triple knockout of the above three genes were performed respectively, to obtain strains TG-5 (SLC1 knock-out), TG-6 (ALE1 knock-out), TG-7 (LOA1 knock-out), TG-8 (SLC1 and ALE1 knock-out), TG-9 (SLC1 and LOA1 knock-out), TG-10 (ALE1 and LOA1 knock-out) and TG-11 (SLC1, ALE1 and LOA1 knock-out).

Figure 3:
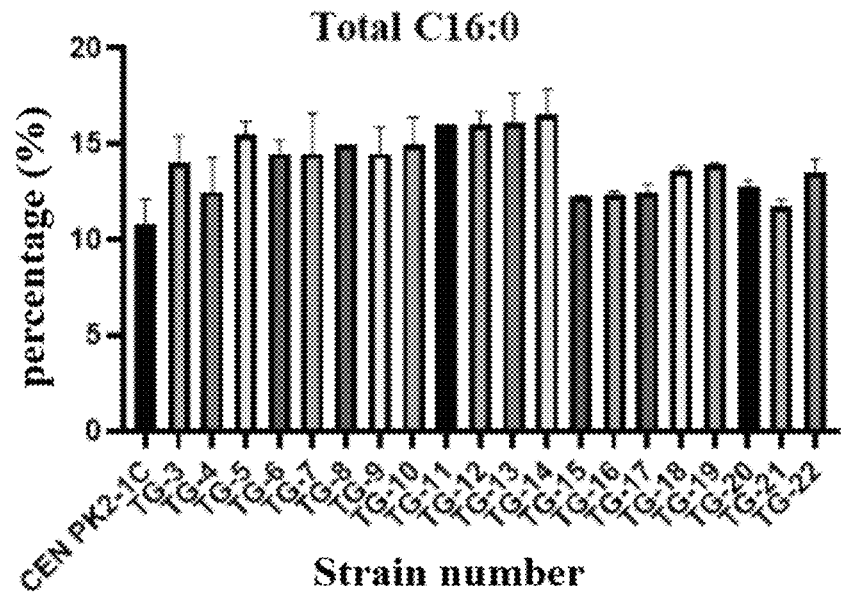
FIG. 3 Relative content of C16:0 in total fatty acids and Sn-2 position in different strains.
Figure 3:
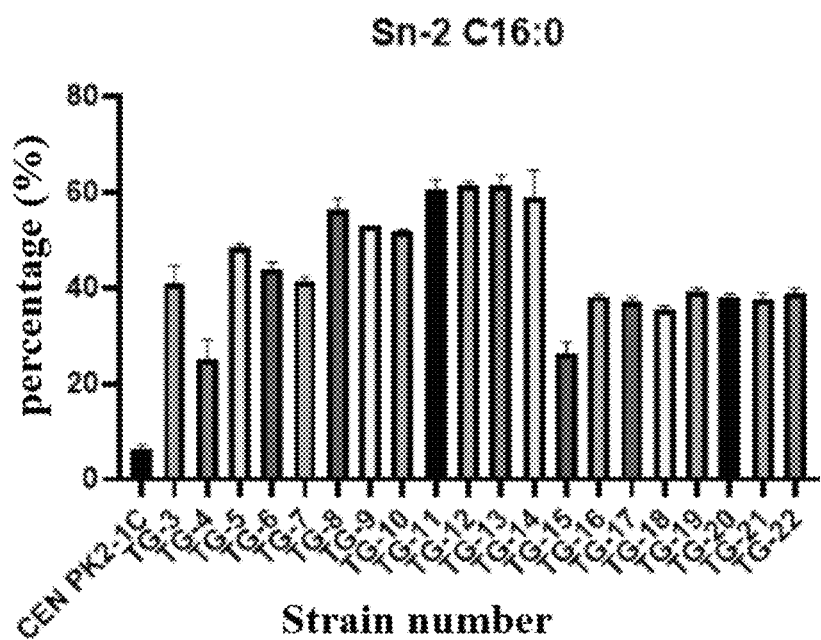

The relative content of C16:0 at total fatty acids and Sn-2 position of strains TG-5 to TG-11 were detected. The results are shown in FIG. 3. The C16:0 content in total fatty acids of strain TG-11 is the highest, and the relative content of C16:0 at Sn-2 is up to 60% or more.

On the basis of strain TG-11, the genes related to the hydrolysis pathway of triacylglycerol in Saccharomyces cerevisiae were knocked out. The primers were designed following the above method. After amplification, the upstream and downstream homologous arms of TGL3 (F19, R19 and F20, R20), TGL4 (F21, R21 and F22, R22) and TGL5(F23, R23 and F24, R24) genes and defective expression frame fragments (F25-F27 and R25-R27) were obtained. These three gene knock-out expression frames were transferred into strain TG-11 to obtain strains TG-12 (TGL3 knock-out), TG-13 (TGL3 and TGL4 knock-out) and TG-14 (TGL3, TGL4, and TGL5 knock-out).

The relative content of C16:0 at total fatty acids and the Sn-2 position of strains TG-12 to TG-14 were detected. The results are shown in FIG. 3. The final detection results show that the total fatty acid content of strain TG-14 is slightly increased compared with TG-11, and the relative content of C16:0 at the Sn-2 position of TAG is increased to 60%. In the above process, the constructed gene integration frame was transformed into competent cells of Saccharomyces cerevisiae by lithium acetate transformation. Colonies were picked up for PCR verification and some transformants verified to be correct by PCR were used for sequencing verification.

Example 3. Production of Human Milk Lipid Substitute Through Fermentation by Recombinant Saccharomyces cerevisiae In the invention, all recombinant Saccharomyces cerevisiae strains were used for fermentation through the following process. The recombinant Saccharomyces cerevisiae strain was streaked with amino-free nitrogen source plates (lacking the amino acid corresponding to the deficient type), and cultured at 30° C. until a large number of colonies were grown.

A single colony was picked to a seed culture medium (any culture medium selected from a sterile medium with no amino nitrogen source, a YPD sterile medium with limited nitrogen source, an inorganic salt sterile medium, and a soybean peptone sterile medium with limited nitrogen source where glucose is used as a carbon source is used as a fermentation medium), cultured at 30° C. and 220 rpm for 18-20 h to the logarithmic phase of cell growth.

The seed culture was inoculated into the fermentation medium (any culture medium selected from a sterile medium with no amino nitrogen source, a YPD sterile medium with limited nitrogen source, an inorganic salt sterile medium, and a soybean peptone sterile medium with limited nitrogen source where glucose is used as a carbon source is used as a fermentation medium) according to an initial inoculation amount of 2-5%, cultured at 30° C. and 220 rpm for 72 h. After 72 h, the culture was stopped, and the yeast cells after fermentation were centrifuged, and freeze-dried for subsequent detection and analysis.

Example 4. Extraction and Detection of Human Milk Lipid Substitute Produced by Recombinant *Saccharomyces cerevisiae*

In the invention, the lipid in all the recombinant *Saccharomyces cerevisiae* strains were extracted through the following process. Tripentadecanoin was added to freeze-dried cells as an internal standard. Methanol and glass beads were added for shaking and crushing the cells, and then the crushed solution was transferred to a new volumetric flask. Then, added the Chloroform, the solution was ultrasonicated in a water bath for 10 min. The supernatant after ultrasonic treatment was transferred to a new volumetric flask, 1.5 ml of methanol/chloroform solvent was added again for extraction. This step was repeated twice. The obtained lipid extracts were combined, and 2.5 ml of chloroform and 3 ml of NaCl aqueous solution were added to the combined solution. The sample was shaken vigorously, and centrifuged at 10000 rpm for 5 min. The upper liquid was discarded, and the lower organic phase was transferred to a new glass tube. The organic phase was blown to dryness with a nitrogen blower and then redissolved in n-hexane. Thin-layer chromatography was used to separate the extracted lipid. The developing agent was n-hexane:ether: acetic acid (70:30:1, v:v:v). Bromothymol blue was used to stain the lipid on the chromatographic plate. According to the staining results, the triglyceride band was taken by a sampler. Then the separated triglyceride sample was transferred to a 10 ml centrifuge tube, and 0.2 ml of n-hexane was added to the test tube. Then 50 mg of pancreatic triglyceride lipase and 2 ml of Tris-HCL (pH=8) buffer were added and shaken carefully. Then 0.5 ml of sodium cholate solution and 0.2 ml of calcium chloride solution were added. The centrifuge tube was capped and shaken carefully. Then the centrifuge tube was allowed to stand in a water bath at 40° C. for 5 min, and the centrifuge tube was shaken by hand. After standing in the water bath, the centrifuge tube was vibrated on a vibrator for 2 min. Then 1 ml of hydrochloric acid solution (6 mol/L) and 1 mL of diethyl ether were added. The centrifuge tube was capped and shaken vigorously for 10 s. After centrifugation at 4000 rpm for 4 min, the organic phase was pipetted, blown with nitrogen to 200 µL, and then determined by GC-MS. The gene localization results are shown in FIG. 1, the results of thin-layer chromatography are shown in FIG. 2, and the C16:0 content is shown in FIG. 3.

Figure 2:
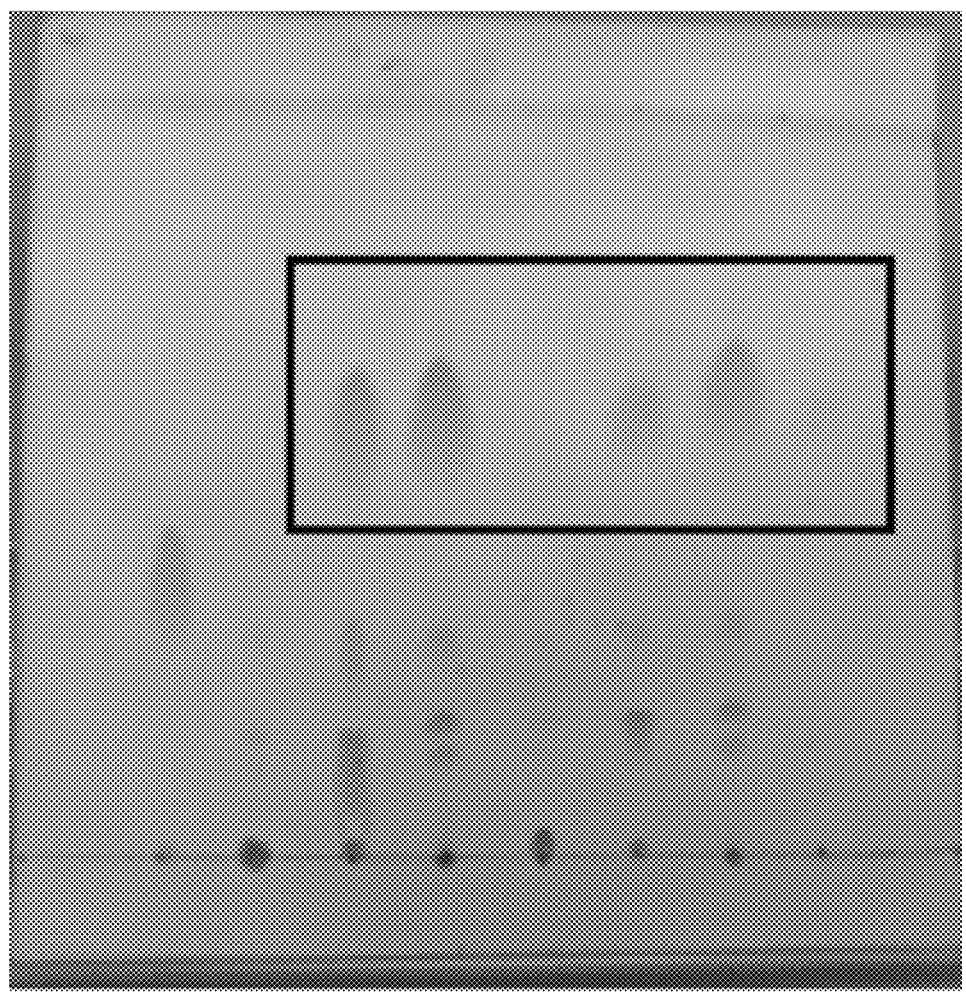
FIG. 2 The triacylglycerol separated by thin-layer chromatography.

As can be seen from FIG. 1, when the heterologous gene CrlPAAT1 was directly integrated into the genome of *Saccharomyces cerevisiae*, the expression level of the gene was low. The expression of the mCrlPAAT1 gene, obtained by knocking out the signal peptide of the heterologous gene itself, is significantly increased in *Saccharomyces cerevisiae*, and it is found that the gene is mainly expressed freely in the cytoplasm. The rmCrlPAAT1 gene is obtained after a signal peptide is added to the C-terminal of the mCrlPAAT1 gene, and is highly expressed in *Saccharomyces cerevisiae* and localized to the endoplasmic reticulum.

Comparative Example 1

The lysophosphatidic acid acyl transferase was replaced by the following sequence (1), its own localization signal peptide (having a sequence as shown in SEQ ID NO: 21) was knocked out, and the signal peptide HDEL was added to the C terminal of the obtained gene following specific steps as described in Example 1 to obtain strain TG-15.

The lysophosphatidic acid acyl transferase was replaced by the following sequence (2), and the signal peptide HDEL was added to the C terminal of the obtained gene following specific steps as described in Example 1 to obtain strains TG-16 and TG-17, respectively.

(1) *Brassica*-derived lysophosphatidic acid acyltransferase LPAT1 (NCBI Reference Sequence: AF111161), the gene sequence as shown in SEQ ID NO: 1;

(2) *Homo sapiens*-derived lysophosphatidic acid acyltransferase AGPAT1 (NCBI Reference Sequence: NC_000006.12) and AGPAT2 (NCBI Reference Sequence: CAH71722.1), the gene sequence as shown in SEQ ID NO: 2 and SEQ ID NO: 3, respectively.

Comparative Example 2

Replace the signal peptide HDEL with the following signal peptide: (1) SRP14 (having a gene sequence as shown in SEQ ID NO: 9), (2) SRP54 (having a gene sequence as shown in SEQ ID NO: 10), (3) CYB5 (having a gene sequence as shown in SEQ ID NO: 11), (4) SEC 12 (having a gene sequence as shown in SEQ ID NO: 12), or (5) FEHDEL (having a gene sequence as shown in SEQ ID NO: 14), following specific steps as described for strain TG-3 in Example 1, to obtain strains TG-18 to TG-22 respectively.

Apparently, the above-described embodiments are merely examples provided for clarity of description and are not intended to limit the implementations of the present invention. For those of ordinary skill in the art, on the basis of the above description, other changes or changes in various forms can also be made. It is not necessary and impossible to exhaustively list all the implementation manners here. The obvious changes or modifications derived therefrom are still within the protection scope of the present invention.

What is claimed is:

1. A *Saccharomyces cerevisiae* strain for producing a human milk lipid substitute, wherein in the *Saccharomyces cerevisiae* strain, a lysophosphatidic acid acyltransferase CrlPAAT1 is expressed, SLC1, ALE1 and LOA1 genes encoding lysophosphatidic acid acyltransferase are knocked out, and TGL3, TGL4 and TGL5 genes encoding triglyceride lipase are knocked out; and in the lysophosphatidic acid acyltransferase CrlPAAT1, a self-localization signal peptide is knocked out, and an endoplasmic reticulum localization signal peptide is connected to the C terminal, wherein the lysophosphatidic acid acyltransferase CrlPAAT1 has a heterologous nucleotide sequence as shown in SEQ ID NO: 4.

2. The *Saccharomyces cerevisiae* strain according to claim 1, wherein the self-localization signal peptide of the lysophosphatidic acid acyltransferase CrlPAAT1 has a nucleotide sequence as shown in SEQ ID NO: 8.

3. The *Saccharomyces cerevisiae* strain according to claim 1, wherein the endoplasmic reticulum localization signal peptide has a nucleotide sequence as shown in SEQ ID NO: 13.

4. The *Saccharomyces cerevisiae* strain according to claim 1, wherein plasmid pMHyLp-LEU is used as an expression vector for the gene encoding the lysophosphatidic acid acyltransferase CrlPAAT1.

5. The *Saccharomyces cerevisiae* strain according to claim 1, wherein SLC1 has a nucleotide sequence as shown in SEQ ID NO: 15, ALE1 has a nucleotide sequence as shown in SEQ ID NO: 16, and LOA1 has a nucleotide sequence as shown in SEQ ID NO: 17.

6. The *Saccharomyces cerevisiae* strain according to claim 1, wherein TGL3 has a nucleotide sequence as shown in SEQ ID NO: 18, TGL4 has a nucleotide sequence as shown in SEQ ID NO: 19, and TGL5 has a nucleotide sequence as shown in SEQ ID NO: 20.

7. The *Saccharomyces cerevisiae* strain according to claim 1, wherein the *Saccharomyces cerevisiae* strain is constructed with *Saccharomyces cerevisiae* CEN PK2-1C, W303, FY1679 or BY4743 as a starting strain.

8. A method of preproducing a human milk lipid substitute, comprising:

providing the *Saccharomyces cerevisiae* strain according to claim 1; and using the *Saccharomyces cerevisiae* strain to produce the human milk lipid substitute.

9. The method according to claim 8, further comprising: using glucose as a substrate to produce the human milk lipid substitute by fermentation.

\* \* \* \* \*

SEQUENCE LISTING

```
Sequence total quantity: 75
SEQ ID NO: 1            moltype = DNA  length = 1173
FEATURE                 Location/Qualifiers
source                  1..1173
                        mol_type = other DNA
                        organism = synthetic construct
SEQUENCE: 1
gttttagctc gcgagattcc gccatggatg tcgcttctgc tcggggggtc tcctcacatc   60
ctccatatta tagcaaaccc atttgttcat cacagtcatc gttgattcgg attccgatca  120
gtaaaggatg ttgctttgct cgttcttcga acttgattac ttcccttcat gctgcttcga  180
gaggggtgac aaggcgtact agtggtgtac aatggtgtta ccgttctatt agatttgacc  240
ctttcaaagt taatgataag aactcaagaa ctgtgactgt gagatcggat ctttcaggag  300
ctgcaacccc tgaatctact tatccagaac cagagattaa gttgagctca agactcagag  360
ggatatgctt ctgtctcgtt gctggcatct ccgccattgt tctcatcgtc ctgatgatca  420
ttggccatcc cttcgtcctt ctatttgatc gttacaggag aaagttccat cacttcattg  480
```

```
ctaagctttg ggcttccata agcatctacc cgttttacaa aacagacatc caaggtttgg    540
agaatctgcc gtcgtcagac actccttgtg tatacgtttc gaaccaccaa agctttctgg    600
atatatacac acttctcagc cttggccaaa gctataagtt catcagcaag acagggatat    660
tcgttattcc tgtcatcggt tgggctatgt ccatgatggg ggttgttccc ttgaagagga    720
tggacccaag aagccaagtg gattgcttaa aacgctgcat ggaactagtg aagaagggag    780
cttccgtctt tttcttccca gagggaacga ggagtaagga tggtcggtta ggtcctttca    840
agaaggggc ttttacgata gcagctaaga caggagttcc agtggtgcca ataacgctga    900
tgggaacagg gaagatcatg ccgacgggta gtgaaggtat actgaatcat ggggatgtga    960
gagtgatcat ccacaagccg atatatggaa gcaaagctga tgttctttgc gaagaggcga    1020
gaaacaagat agctgaatct atgaatctct tgagttgaaa cgtttgtttt ttaagcagtg    1080
tctctatgaa caatgagaag gctaaaccat ttttacatgt cagttttatt gtttaaaata    1140
aaatttaggc ttttcaaaaa aaaaaaaaaa aaa                                 1173

SEQ ID NO: 2            moltype = DNA   length = 3255
FEATURE                 Location/Qualifiers
source                  1..3255
                        mol_type = other DNA
                        organism = synthetic construct
SEQUENCE: 2
atggagggga acaacacaca ccagggcctc tcaggggac ggggggtagg agaccatcag     60
gacaaacacg tgagtacatg gagggaaca acacacacca gggcctctca ggggacggg     120
gggtaggaa ccatcaggac aaaacacgtgg gtacatggaa ggaacaaca cacaccaggg    180
cctctcagcg ggacaggggg taggagacca tcaggacaaa cacgtggata catggagggg    240
aacaacacac accagggcct ctcagcggga caggggtag agaccatca ggacaaacac     300
gtgggtacat ggagggaac aacacacacc agggcctctc aggggacag gggtaggag     360
accatcagga caaacacgtg gtacatggaa gggaacaac acacaccagg gcctctcagg    420
gggacagggg taggagacca tcaggacaaa cacgtgggta catggagggc aacaacacac    480
accagggcct ctcaggggga caggggtag gagaccatca gtacaaacac gtggatacat    540
ggaggggaac agcacacacc agggcctctc agcgggacag gggtaggaga ccatcaggac    600
aaacacgtgg gtacatggag gggaacaaca cacaccaggg cctctcaggg ggacaggggg    660
taggagacca tcaggacaaa cacgtgggta catggagggg aacaacacac caggggcct    720
ctcagggga cggggggtag gagaccatca ggacaaatag ctaatgcatg cagggcctca    780
tacctaggtg atgggttgat gggtgcagca accaccatg cacacattt acctatgtat    840
caaacctata ctttctgcac gtgtatccca gaacataaaa taaaattaaa aaaatatata    900
cactgattca tgatctccctt tctctccttc tgaaacactc tttaaaactt tttagcattt    960
ccccctctgt cttccatgtc tcctaactac atgtttctta tttttcatgt ctttattcct    1020
gtgttcattt tggatagccc cttctgacct atattacagt ttactagttc actcttcaac    1080
tgcttctaac atactaatat tctgttaaaa ccattcattt gggtttaaat ttcaattatg    1140
ttattctcta tggacattct attttgtttc ttttaatctt cttggccatt ctctagagtt    1200
tcctgttcca ttatgatat tttaattttt tgttttactt taaacatact aaatatagtt     1260
atttatttt atttctgta tctgatactt tcaataactg cagtctttgc tagtcttttt      1320
tctgtgctct tgctcatagt ttttttcgtt tgttttcatg attagaaaga gagagaagaa    1380
ggagagtaaa gggaggagga ggaggaggag aaaagaagaa aagaagacaga                1440
aaaaaaggaa gttggttcta acgtttctct aacaactggc ttcagtgaaa cactcccacc    1500
ttgtggattt taggttatt gaaattaacc agtcttctgg gtgcagcaca ccaacatggc     1560
acatgtatac atatgtaaca aacctgcact tgtgcacat gtacctaaa acttaaaagta    1620
caataaaaa taaataaaa agctacacaa atttaaaaaa aagaaatca acctaattcc      1680
tagattacca cctcttgatt caaatgcttt aaatctaggc ttttcatctg agtcttctt    1740
tttagttatt ctgtttatct tcaaacacact cctgctttga atcattcaaa atctacctcc    1800
ctccctctgt ttgactacca tcaatttttt tgctcattcc taatgcatta atctattagc    1860
tgtgaatatc caaaaaccct catttcactg aatctttgac agacccctttt gcatcctctt    1920
gttcttctaa ttatttcctc agaaacttta tgttctcttt tctttacaag catgtcatag    1980
tttatatata atgtgtgtat tgttttttata tacctata tatagcctct ttttaaaagc    2040
actatacacc atgctttgaa atatattcta aaatcaggta gcatgaaaat ggaaactaaa    2100
catactaaaa catatgggat gcaacaaaag cagttataag agggacattt atagcaataa    2160
atgcctacat caaaaaagaa aaaaagatc tcaaataagc aacctaatat tatgcctaaa    2220
ggagcgagaa aattagagaa caatacaagc ccaaagatag cagaaggaaa caaataacaa    2280
agatcagagc agaaataata aatagaaac tgaaaatttc aataaaaata agaattgttt    2340
tttgaaaaga taaacaaaat taacaaattc ttacatagac taagaaaaaa gaaaacaaac    2400
tcagaagtga aagaagagac attacaactg ataccacaga agttaaaaaa tcataacata    2460
ctactataaa caattattca ccagcaaatt agataaccta gaagaaattg ataaactcgt    2520
accaaaactg aatcatgaag aattcaaaat ttagaagaaa tcatgaataa ggaaattaaa    2580
tcaccaatga aagttctctc ataaaagaaa gacccaggat tgaatggctt ggtggctgaa    2640
ttccaacaaa cacttagatg actaacacca atccttccca aaaaaaatga                2700
agaagaggaa tacttccaaa ttcattttc aaaaccagca ttaccctgat accaaaacca    2760
gagaaggaca ctataataaa aatatatggc agaccaatac tcctgatgaa cttggatgga    2820
aaaaccttca gccaaatatt agcaaatatt atttttaaaa aaacacagca aaaaaattcg    2880
ccatgcttaa gtgggattca tccctgggaa gcttattagt cttatttgat tcgtgtaatc    2940
agaaaatttc tatgtctagt gaagagaaat gagagccata gcaccctcaac    3000
aaatgtccag gcttgagcca gttaacaaat acaagtccctt caaatacaaa aaagactgtg    3060
aaagaaaata gaacagatca atgaaactaa gaattttgttc tttgaaaaga taaaactgac    3120
aaaccattag ctagactaga aaatgagag aatactcaaa gcaataaaat cagaaatgaa    3180
agaggaaata ttgcaactaa taccacgaaa atacagagga tcataagagg ccactataaa    3240
caattacaag ccaac                                                     3255

SEQ ID NO: 3            moltype = DNA   length = 837
FEATURE                 Location/Qualifiers
source                  1..837
                        mol_type = other DNA
```

-continued

```
                        organism = synthetic construct
SEQUENCE: 3
atggcctcag gactcccacc cccacagcgt ggccagggc ttccttgggg cccgccaagt    60
tcctgggacc ctcccaggct agtcagggct cccagcagga gccccctgca ccgagacggc   120
cgtgtccccct gctccatggg accacagcac ccactgtcac acacacacag ccaccgtccc   180
atcaggcacc cacatccccg tggggccccgg ctcagccagg ggttgccagc ctcccagggt   240
atccttgaca gctgggggag gctggccttg gccccatctc tctctacccc actgctgggg   300
gtcggccctc ccacttcctc tcctcttccc ctaaggtcct gtcacaatga ggagctccca   360
ggggccggcg ctgcagccac cctccccggg caggctggag ccggccttcc ttccacctcg   420
ccctccgctt cccacgggta agctgctcgc aaggcagccg gcacgctcgg gtcacgaggt   480
caagggcagc aggagcgacc agggagttgc agtcaccctg cccgtgcca caacctcgtt    540
cacaggaggg aaatcaggca ggcccagaga cggcaagcaa cctgtataag atcacacagc   600
cagcgcaggg tgaggcctgg gctctgggca cctgactctc acgtgtcggt tgcctctgct   660
cctccctccg tcagtgctgg ctgccccctg aagctgtcat ccaggggacca gcaaacagaa   720
gtgtctgaat gaggcaacag catggccccc gccccagcag ttaaaggttt gaggcagatc   780
cccataggac tttgggccaa cacctccaaa tctctgagcg ggacagggag atggtga      837

SEQ ID NO: 4        moltype = DNA   length = 975
FEATURE             Location/Qualifiers
source              1..975
                    mol_type = other DNA
                    organism = synthetic construct
SEQUENCE: 4
caaaaaagat ctcaaaacag aagaaccaac ccaagcagcc aaaaccaaag caacaacttg    60
ttgagcagca ccagtagcag ccaaagctgc agccaaacct ctccaagaac cataacaaac   120
accagcaaaa accaaaatag aaaccaaagt aatagccaat tgttgaaccc acatagatga   180
agaataagaa taagcttgtg gaccaggcat agaaaatctt ggaacatttt tcaaatcttc   240
caaaccataa gtagcagccc aacaagaatc ccaagtagct tgcaaatcag taaaaaaagc   300
ttcaaaattt ggataatcag cagatttcaa aaccttagaa aaagtagtaa cacaagttct   360
accaaaatga acagattgag attttttcaga caaaacttca tcttttacctc tagtaacaac   420
aattttgaaca ggcaattttc tagaatgagc ataatgcaac atacctcttt tcaatggcaa   480
agaagcaggt ttagtagatc tatgaccttc aggataaacc aacaaccag gaacatgaga    540
agaacccaaa gtttgatcca accaagcatt aaaagcttct ttatcagcaa tagtacctct   600
cttaaacaaa acaataccctt tcaaaatcat gcaagaagta caaaaacag ggaaaacaaa    660
ataaaccaac catctagaca ttaaagcagc tctaccttca gtcaaataag catcaataaa    720
aaaatcagcc caagatctat gattacacaa atacaaacat ggaccaccttt tatacaaagt   780
atgttcacca gcttgcaaca agtaactct aaaataagca accaaagctc tagcccaatc    840
caacatatca tttcttttac ccaaagaagc gaatctgatt ctatataaaa tagcaaagat   900
tggtaaagac caataaaaaa caaaaacaga aaacaagaaa gatggtaaac ccaaccattt   960
agtcaaaaca gacat                                                   975

SEQ ID NO: 5        moltype = DNA   length = 4538
FEATURE             Location/Qualifiers
source              1..4538
                    mol_type = other DNA
                    organism = synthetic construct
SEQUENCE: 5
cttgctgaaa agatgatgtt ctgaggtatt cgtatcgcta gcttgatacg cttttaacaa    60
aagtaagctt tcgtttgca ggtttggtta cttttctgta cgagatgata tcgctaagtt   120
tatagtcatc tgtgaaattt ctcaaaaacc tcatggtttc tccatcaccc atttttcatt   180
tcatttgccg ggcggaaaaa aaaaggaaa aaaaaaaaa aaaaaataa atgacacatg    240
gaaataagtc aaggattagc ggatatgtag ttccagtccg ggttatacca tcacgtgata   300
ataaatccaa atgagaatga gggtgtcata tctaatcatt atgcacgtca agattctccg   360
tgactatggc tcttttctga agcatttttc gggcgcccgg tggccaaaaa ctaactccga   420
gcccgggcat gtcccggggt tagcgggccc aacaaagcg cttatctggt gggcttccgt   480
agaagaaaaa aagctgttga gcgagctatt tcgggtatcc cagccttctc tgcagaccgc   540
cccagttggc ttggctctgg tgctgttcgt tagcatcaca tcgcctgtga caggcagagg   600
taataacggc ttaaggttct cttcgcatag tcggcagctt tctttcggac gttgaacact   660
caacaaacct tatctagtgc ccaaccaggt gtgcttctac gagtcttgct cactcagaca   720
cacctatccc tattgttacg gctatgggga tggcacacaa aggtggaaat aatagtagtt   780
aacaatatat gcagcaaatc atcggctcct ggctcatcga gtcttgcaaa tcagcatata   840
catatatata tggggggcaga tcttgattca tttattgttc tattccatc tttcctactt    900
ctgtttccgt ttatattttg tattacgtag aatagaacat catagtaata gatagttgtg   960
gtgatcatat tataaacagc actaaaacat tacaacaaag caggaaacag ctatgaccat   1020
gattacgcct aggataactt cgtatagcat acattatacg aagttatgac gacagagacc   1080
gggttggcgg cgcatttgtg tcccaaaaaa cagccccaat tgcccccaatt gaccccaaat   1140
tgacccatta agcaaggatt ttcttaactt cttcggcgac agcatcaccg acttcggtgg   1200
tactgttgga accaccctaaa tcaccagttc tgataacctgc atccaaaacc ttttttaactg   1260
catcttcaat ggccttacct tcttcaggca agttcaatga caatttcaac atcattgcag   1320
cagacaagat agtggcgata gggtcaacct tattctttgg caaatctgga gcagaaccgt   1380
ggcatggttc gtacaaaacca aatgcggtgt tcttgtctgg caaagaggcc aaggacgcag   1440
atggcaacaa acccaaggaa cctgggataa cggaggcttc atcggagatg atatcaccaa   1500
acatgttgct ggtgattata ataccattta ggtgggttgg gttcttaact aggatcatgg   1560
cggcagaatc aatcaattga tgttgaacct tcaatgtagg gaattcgttc ttgatggttt   1620
cctccacagt ttttctccat aatcttgaag aggccaaaac attagcttta tccaaggacc   1680
aaataggcaa tggtggctca tgttgtaggg ccatgaaagc ggccattctt gtgattcttt   1740
gcacttctgg aacggtgtat tgttcactat cccagcgac accatcacca tcgtcttcct   1800
ttctcttacc aaagtaaata cctcccacta attctctgac aacaacgaag tcagtacctt   1860
tagcaaattg tggcttgatt ggagataagt ctaaaagaga gtcggatgca aagttacatg   1920
```

```
gtcttaagtt ggcgtacaat tgaagttctt tacggatttt tagtaaacct tgttcaggtc   1980
taacactacc ggtaccccat ttaggaccac ccacagcacc taacaaaacg gcatcaacct   2040
tcttggaggc ttccagcgcc tcatctggaa gtgggacacc tgtagcatcg atagcagcac   2100
caccaattaa atgattttcg aaatcgaact tgacattgga acgaacatca gaaatagctt   2160
taagaacctt aatggcttcg gctgtgattt cttgaccaac gtggtcacct ggcaaaacga   2220
cgatcttctt aggggcagac ataggggcag acattagaat ggtatatcct tgaaatatat   2280
atatatattg ctgaaatgta aaaggtaaga aagttagaa agtaagacga ttgctaacca   2340
cctattggaa aaaacaatag gtccttaaat aatattgtca acttcaagta ttgtgatgca   2400
agcatttagt catgaacgct tctctattct atatgaaaag ccggttccgg cctctcacct   2460
ttccttttc tcccaatttt tcagttgaaa aaggtatatg cgtcaggcga cctctgaaat   2520
taacaaaaaa tttccagtca tcgaatttga ttctgtgcga tagcgcccct gtgtgttctc   2580
gttatgttga ggaaaaaaat aatggttgct aagagattcg aactcttgca tcttacgata   2640
cctgagtatt cccacagtta actgcggtca agatatttct tgaatcaggc gccttagacc   2700
gctcggccaa acaaccaatt acttgttgag aaatagagta taattatcct ataaatataa   2760
cgttttaggg taccgactag ttccatggcc tgtcccacg ttgccggtct tgcctcctac   2820
tacctgtcca tcaatgacga ggttctcacc cctgcccagg tcgaggctct tattactgag   2880
tccaacaccg gtgttcttcc caccaccaac ctcaagggct ctcccaacgc tgttgcctac   2940
aacggtgttg gcatttaggc aattaacaga tagtttggc gtgataattc tcttaacctc   3000
ccacactcct ttgacataac gatttatgta acgaaactga aatttgacca gatattgttg   3060
taaatagaaa atctggcttg taggtggcaa aatgcggcgt ctttgttcat caattccctc   3120
tgtgactact cgtcatccct ttatgttcga ctgtcgtatt tcttattttc catacatatg   3180
caagtgagat gcccgtgtcc gttatcaaat ctagttaata acttcgtata gcatacatta   3240
tacgaagtta tgctagcgtc cggagcggcc gcgcatgcaa gtcgaccttg cactggccga   3300
tcgttttaat agcttcaaaa tgtttctact ccttttttac tcttccagat tttaggagtt   3360
agacaacctg aagtctaggt ccctatttat tttttatag ttatgttagt attaagaacg   3420
ttatttatat ttcaaatttt tcttttttt ctgtacagac gcgtgtaacg atgtaacatt   3480
atactgaaaa ccttgcttga gaaggttttg ggacgctcga aggctttaat ttgcggccgt   3540
atcacattac aataacaaaa ctgcaactac cataaaaaaa aattgaaaaa tcataaaatta   3600
aaaaaaaaaa aatcaattga attttttttt ttcatgatta cgttttgaca ttttttccttt   3660
tttttctct tattacgatt tacctttttt atttatttt ttcattttag tattttattc   3720
ttcgttattt atgtatagaa attttcatt tcatttagat tcagatttgg ttatctttt   3780
tcattatata tcttttgcac taagtttcaa cttaagttct atttttatt tttttttct   3840
gggccctgga gcaatagata tgggatggct tactgcatct cttcaaaatt tcacagtcat   3900
gctcacccttt aagttctcaa cctttttagtt tttttttta tttttgtatgg           3960
catactaact atacaaatat ttatatgtac atttatacag taacctatta tttaccgata   4020
ttcaccggta ttttacttta atagatgctg gtaataacga aaaaaattga taactcccac   4080
cgacaattga gaaaaaaagc aaaaaaggaa aaagggaag cacgaattaa tacattctgt   4140
gtatttatct tttttatctt cagttttcct ccaatctatg ggcggccatt aagtatgtct   4200
attattcttg gcccttcagt cttctttgga tttcaatgtc ttgttggatt agaagtcatc   4260
accactttca gcaatcaaag ccatgatcat tctgtacaag tagaagaaga acatcaataa   4320
gtggaaacct aactttagga aactctccct tttatgtttg cctaaagttc tgaatatttc   4380
ggtagcatcc aaaagttgaa ctttattgta gatcttgttt agattgtaag ctagaactgg   4440
taagttcaat aaaaatacaa accagtaacc gttcagtaag aatagtaatg acaaagcacc   4500
atgcaaggcg gcttcagggg taattaactt gttaactt                          4538

SEQ ID NO: 6          moltype = DNA   length = 653
FEATURE               Location/Qualifiers
source                1..653
                      mol_type = other DNA
                      organism = synthetic construct
SEQUENCE: 6
attaatttca caggtagttc tggtccattg gtgaaagttt gcggcttgca gagcacagag    60
gccgcagaat gtgctctaga ttccgatgct gacttgctgg gtattatatg tgtgcccaat   120
agaaagagaa caattgaccc ggttattgca aggaaaattt caagtcttgt aaaagcatat   180
aaaaatagtt caggcactcc gaaatacttg gttggcgtgt ttcgtaatca acctaaggag   240
gatgttttgg ctctggtcaa tgattacggc attgatatcg tccaactgca tggagatgag   300
tcgtggcaag ataccaaga gttcctcggt ttgccagtta ttaaaagact cgtatttcca   360
aaagactgca acatactact cagtgcagct tcacagaaac ctcattcgtt tattcccttg   420
tttgattcag aagcaggtgg gacaggtgaa cttttgatt ggaactcgat ttctgactgg   480
gttggaaggc aagagagccc cgaaagctta cattttatgt tagctggtgg actgacgcca   540
gaaaatgttg gtgatgcgct tagattaaat ggcgttattg gtgttgatgt aagcggaggt   600
gtggagacaa atggtgtaaa agactctaac aaaaatagcaa atttcgtcaa aaa           653

SEQ ID NO: 7          moltype = DNA   length = 1263
FEATURE               Location/Qualifiers
source                1..1263
                      mol_type = other DNA
                      organism = synthetic construct
SEQUENCE: 7
agagcttggt gagcgctagg agtcactgcc aggtatcgtt tgaacacggc attagtcagg    60
gaagtcataa cacagtcctt tcccgcaatt ttcttttttct attactcttg gcctcctcta   120
gtacactcta tatttttta tgcctcggta atgattttca ttttttttttt tcccctagcg   180
gatgactctt ttttttcttt agcgattggc attatcacat aatgaattat acattatata   240
aagtaatgtg atttcttcga agaatatact aaaaaatgga caggcaagat aaacgaaggc   300
aaagatgaca gagcagaaag ccctagtaaa gcgtattaca aatgaaacca agattcagat   360
tgcgatctct ttaaagggtg gtcccctagc gatagagcac tcgatcttcc cagaaaaaga   420
ggcagaagca gtagcagaac aggccacaca atcgcaagtg attaacgtcc acacaggtat   480
agggtttctg gaccatatga tacatgctct ggccaagcat tccggctggt cgctaatcgt   540
tgagtgcatt ggtgacttac acatagacga ccatcacacc actgaagact gcgggattgc   600
```

```
tctcggtcaa gcttttaaag aggccctact ggcgcgtgga gtaaaaaggt ttggatcagg    660
atttgcgcct ttggatgagg cacttttcca gagcggtggta gatctttcga acaggccgta    720
cgcagttgtc gaacttggtt tgcaaaggga gaaagtagga gatctctctt gcgagatgat    780
cccgcatttt cttgaaagct ttgcagaggc tagcagaatt accctccacg ttgattgtct    840
gcgaggcaag aatgatcatc accgtagtga gagtgcgttc aaggctcttg cggttgccat    900
aagagaagcc acctcgccca atggtaccaa cgatgttccc tccaccaaag gtgttcttat    960
gtagtgacac cgattattta aagctgcagc atacgatata tatacatgtg tatatatgta    1020
tacctatgaa tgtcagtaag tatgtatacg aacagtatga tactgaagat gacaaggtaa    1080
tgcatcattc tatacgtgtc attctgaacg aggcgcgctt tccttttttc ttttttgctt    1140
ttcttttttt ttctcttgaa ctcgataggg taccgactag ttccatggcc tgtcccacg    1200
ttgccggtct tgcctcctac tacctgtcca tcaatgacga ggttctcacc cctgcccagg    1260
tat                                                                  1263

SEQ ID NO: 8           moltype = DNA  length = 420
FEATURE                Location/Qualifiers
source                 1..420
                       mol_type = other DNA
                       organism = synthetic construct
SEQUENCE: 8
ttgatccaac caagcattaa aagcttcttt atcagcaata gtacctctct taaacaaaac    60
aataccttc aaaatcatgc aagaagtaca aaaaacaggg aaaacaaaat aaaccaacca    120
tctagacatt aaagcagctc taccttcagt caaataaaaa aatcagccca                180
agatctatga ttacacaaat acaaacatgg accaccttta tacaaagtat gttcaccagc    240
ttgcaacaaa gtaactctaa aataagcaac caaagctcta gcccaatcca acatatcatt    300
tcttttaccc aaagaagcga atctgattct atataaaata gcaaagattg gtaaagacca    360
ataaaaaaca aaaacagaaa acaagaaaga tggtaaaccc aaccatttag tcaaaacaga    420

SEQ ID NO: 9           moltype = DNA  length = 168
FEATURE                Location/Qualifiers
source                 1..168
                       mol_type = other DNA
                       organism = synthetic construct
SEQUENCE: 9
gcaaatactg gctgtttatc accaggtgca tttttatcaa aggttccaga atttttccag    60
actgcgaatg aaaaacatat aactgtgcgt ctaacggcca aaagactcat agaacacgat    120
cctgtggaag ggaatcttga atttgattct accaaccatc ctgactat                 168

SEQ ID NO: 10          moltype = DNA  length = 195
FEATURE                Location/Qualifiers
source                 1..195
                       mol_type = other DNA
                       organism = synthetic construct
SEQUENCE: 10
ttttataatt tcttcaaca tattttttgtt taagccggca ttgttgtttt tcttcttgtc     60
attcattaaa tgagagttgt aaattgaact tgaattacca ctactactac ttccattgga    120
attagaaaac agtagcttca tcttttctga tatttccttt attagtaagc taaccgccac    180
atcgacattt aaatc                                                     195

SEQ ID NO: 11          moltype = DNA  length = 95
FEATURE                Location/Qualifiers
source                 1..95
                       mol_type = other DNA
                       organism = synthetic construct
SEQUENCE: 11
tatctacctc tgaaaaccaa agtaaaggta gtggtacatt ggttgtcata ttggccattt     60
taatgctagg tgttgcttat tatttgttga acgaa                               95

SEQ ID NO: 12          moltype = DNA  length = 129
FEATURE                Location/Qualifiers
source                 1..129
                       mol_type = other DNA
                       organism = synthetic construct
SEQUENCE: 12
agagatggtg tctctttcg ttagaaaatt gtccttcgcg taattgaaaa gcatggaatg      60
caaattgtgc ttataggaga actgtaaaat gtaagaaagc agcacaataa ggatgaagtt    120
ggtgaaaaa                                                            129

SEQ ID NO: 13          moltype = DNA  length = 393
FEATURE                Location/Qualifiers
source                 1..393
                       mol_type = other DNA
                       organism = synthetic construct
SEQUENCE: 13
tcagaacaag cagcacaaca agcagttaat aatgcgggct ggtcagttat ttcagcagca     60
caactgggct atgcgggcaa aacagatgca agaggcacat attatggcga acagcgggc     120
tatacaacag cacaagcaga agttctgggc aaatatgatt cagaaggcaa tctgacagca    180
attggcattt catttagagg cacaagcggc ccgagagaat cactgattgg cgatacaatt    240
ggcgatgtta ttaatgatct gctggcgggc ttcgcccga aaggctatgc agatggctat    300
acactgaaag catttggcca actgctgggc gatgttgcaa aatttgcaca agcacatggc    360
```

```
ctgagcggcg aagatgttgt ggttagcggc cat                          393

SEQ ID NO: 14         moltype = DNA   length = 431
FEATURE               Location/Qualifiers
source                1..431
                      mol_type = other DNA
                      organism = synthetic construct
SEQUENCE: 14
attcactggg cggcctggca gttaattcaa tggcagcaca atcagatgca aattggggcg     60
gcttttatgc acaatcaaat tatgttgcat ttgcatcacc gacacaatat gaagcgggcg    120
gcaaagttat taatattggc tatgaaaatg atccggtttt tagagcactg gatggcacaa    180
cactgacggg cgcatcactg ggcgttcatg atgcaccgca tgcatcagca acaaataata    240
ttgttaattt taatgatcat tatgcatcag atgcatggaa tctgctgccg ttttcaattc    300
tgaatattcc gacatggctg tcatatctgc cgtttttta tcaagatggc ctgatgagag    360
ttctgaattc agagttctat tcactgacag ataaagattc aacaattatt gtgtcaaatc    420
tgtcaaaatgt t                                                        431

SEQ ID NO: 15         moltype = DNA   length = 912
FEATURE               Location/Qualifiers
source                1..912
                      mol_type = other DNA
                      organism = synthetic construct
SEQUENCE: 15
atgagtgtga taggtaggtt cttgtattac ttgaggtccg tgttggtcgt actggcgctt     60
gcaggctgtg gcttttacgg tgtaatcgcc tctatccttt gcacgttaat cggtaagcaa    120
catttggctc agtggattac tgcgcgttgt ttttaccatg tcatgaaatt gatgcttggc    180
cttgacgtca aggtcgttgg cgaggagaat ttggccaaga agccatatat tatgattggc    240
aatcaccaat ccaccttgga tatcttcatg ttaggtagga ttttcccccc tggttgcaca    300
gttactgcca agaagtcttt gaaatacgtc ccctttctgg gttggttcat ggctttgagt    360
ggtacatatt tcttagacag atctaaaagg caagaagcca ttgacaccctt gaataaaggt    420
ttagaaaatg ttaagaaaaa caagcgtgct ctatgggttt ttcctgaggg taccaggtct    480
tacacgagtg agctgacaat gttgcctttc aagaagggtg cttttcattt ggcacaacag    540
ggtaagatcc ccattgttcc agtggttgtt tccaatacca gtactttagt aagtcctaaa    600
tatggggtct tcaacagagg ctgtatgatt gttagaattt taaaacctat ttcaaccgag    660
aacttaacaa aggacaaaat tggtgaattt gctgaaaaag ttagagatca aatggttgac    720
actttgaagg agattggcta ctctcccgcc atcaacgata caaccctccc accacaagct    780
attgagtatg ccgctcttca acatgacaag aaagtgaaca agaaaatcaa gaatgagcct    840
gtgccttctg tcagcattag caacgatgtc aatacccata cgaaggttc atctgtaaaa    900
aagatgcatt aa                                                        912

SEQ ID NO: 16         moltype = DNA   length = 1860
FEATURE               Location/Qualifiers
source                1..1860
                      mol_type = other DNA
                      organism = synthetic construct
SEQUENCE: 16
atgtacaatc ctgtggacgc tgttttaaca aagataatta ccaactatgg gattgatagt     60
tttacactgc gatatgctat ctgcttattg ggatcgttcc cactgaatgc tattttgaag    120
agaattcccg agaagcgtat aggtttaaaa tgttgtttta tcatttctat gtcgatgttt    180
tacttattcg gtgtgctgaa tctagtaagt ggattcagga ccctgtttat tagtaccatg    240
tttacttact tgatctcaag attttaccgt tccaagttta tgccacactt gaattttcag    300
tttgttatgg gtcatttggc aataaaatcat atacacgccc aattccttaa cgaacagact    360
caaactaccg ttgacattac aagttcacaa atggttttag ccatgaaact aacttctttt    420
gcatggtcgt actatgatgg ttcatgcact agcgaaagcg atttcaaaga tttgactgag    480
catcaaaaat ctcgtgctgt cagaggtcat ccacccttat caaagttcct ggcatatgca    540
tttttctatt caacgttgct aactggccca agtttcgatt atgccgattt tgacagctgg    600
ttgaattgtg agatgttccg tgacttgcct gaaagcaaaa agcctatgag aagacaccac    660
cctggtgaaa aagacagat tccaaagaat ggtaaacttg cattatgaaa agttgttcaa    720
ggtcttgctt ggatgatttt aagtacacta ggaatgaagc acttcccgt aaaatacgtt    780
ttggacaaag atggcttccc aacgagatct tttatattca gaatccatta cttattcttg    840
cttggttca tccatagatt caagtactac gctgcctgga ctatttcgga aggatcttgt    900
attttgtgcg gtttgggtta taatggttat gattcaaaga cacaaaagat cagatgggat    960
cgtgtcagaa atattgacat ttggaccgta gaaacggcgc agaatacgcg tgaaatgttg   1020
gaagcatgga atatgaatac taacaagtgg ctaaaataact ctgttttattt acgtgtcaca   1080
aagaagggca aaaaacctgg tttccgctca acttgtttta ctttcctaac ttccgcattt   1140
tggcatggta ccagacctgg gtactatctg acttttgcga caggggcttt gtaccaaaca   1200
tgtggtaaaa tctacagacg caattttaga ccaattttct gcgagaaga tggtgtcact   1260
cctttgcctt ctaaaaaaat ctacgattta gttggcataa atgcaattaa actagcattt   1320
ggttacatgg tgcaaccatt tattatcctt gattgaagc catctttaat gtgatgggc   1380
tctgtttatt tctatgttca tattattgtt gcttctcat ttttcctatt cagaggacca   1440
tatgctaaac aagttactga atttttaaa tccaaacaac ctaaagaaat attcattaga   1500
aaacaaaaga agttggaaaa agatatttct gcaagctctc caaacttggg tggtatatgt   1560
aaggcaaaga ttgaacatga aaagggaaag acagcagaag aagaagaaat gaacttaggt   1620
attccaccaa ttgagttaga aaagtgggac aagctaaagg agaattggga agatttctgc   1680
aaagattaca aagaatggag aaataaaaat ggtcttgaaa tagaagagga aaacctttct   1740
aaagcttttg aaagattcaa gcaggaattt tctaacgctg caagtggatc aggtgaacgt   1800
gtgagaaaaa tgagttttag tggttactca ccaaagccta tttcaaaaaa ggaagagtag   1860

SEQ ID NO: 17         moltype = DNA   length = 903
```

| FEATURE | Location/Qualifiers | |
|---|---|---|
| source | 1..903 | |
| | mol_type = other DNA | |
| | organism = synthetic construct | |

SEQUENCE: 17

| | | |
|---|---|---|
| atggaaaagt acaccaattg gagagacaat ggtacgggaa tagctccatt tctaccaaac | 60 |
| acaatcagga aacctagtaa ggtgatgaca gcgtgtttgt tgggtatcct aggggtgaaa | 120 |
| accattataa tgctaccatt gattatgctg taccttctaa ctggccagaa caacttactg | 180 |
| ggtttgatat tgaagtttac attcagttgg aaagaggaaa ttaccgtgca aggaatcaag | 240 |
| aaacgtgacg taaggaaatc caagcattat ccacagaagg gcaagcttta tatttgcaat | 300 |
| tgtacctcac ctttagatgc ttttttcagtg gtgttattag ctcaagggcc tgttacgttg | 360 |
| ttggtcccat ccaatgacat tgtatacaaa gtttccataa gagaattcat caacttcatc | 420 |
| ctcgccggtg ggttagatat aaaactctat ggccacgagg tagcagagct atctcaattg | 480 |
| ggcaataccg tgaattttat gtttgctgag ggtacctcat gtaatggtaa aagcgtctta | 540 |
| ccgtttagta taaccgggaa aaaacttaaa gaattcatag accttcaat aaccacaatg | 600 |
| aaccccgcaa tggccaaaac taaaaaaattt gaattgcaga ccatccaaat caaaactaat | 660 |
| aaaactgcca tcaccacatt gcccatctcc aatatggagt atttatctag atttctgaac | 720 |
| aagggcatta atgttaaatg caagatcaac gagccacaag tactctcgga taatttagag | 780 |
| gaattacgcg ttgcattaaa cggtggcgca aaatataaac tagtctcacg gaagttagat | 840 |
| gttgaatcta agaggaattt tgtgaaggaa tatatcagcg atcaacgtaa aaagaggaag | 900 |
| tag | 903 |

| SEQ ID NO: 18 | moltype = DNA length = 1929 |
|---|---|
| FEATURE | Location/Qualifiers |
| source | 1..1929 |
| | mol_type = other DNA |
| | organism = synthetic construct |

SEQUENCE: 18

| | | |
|---|---|---|
| atgaaggaaa cggcgcagga atacaaggtg tctgctgtaa taccgaccct tttgaaaaac | 60 |
| tggatactgc gtgtagtgta tgccacattg gaccatatac ctccttttgt gtgggaaatt | 120 |
| ctacatgtca tcaccgatat ttatttcttc tgggttcaaa agctgattaa ctatgtgcgi | 180 |
| ccacactcaa gagtcattta ttataacgct attaagaagt tagatgagtg tgatacgtat | 240 |
| caaatgtggt gtcagcaagc gtccgtagtg atgaaataa caggcgcaaa tttatggcgg | 300 |
| cggaatttct tttcgaggag gtacgacttc aattctgtca ttgaacaata tagcatattg | 360 |
| gaaaatatgt taagggagga gaagtgatgat gtagttaagg agaagtttc gactacaggc | 420 |
| ccttgtatgt tgaggaactt tgcgggtatt ggagataaaa agttgttcac aaaatctttg | 480 |
| atgggtacaa agctacttat tgaacaatat ttgacccgaa ttctagaagg cttggatata | 540 |
| ttaaataatc aaactttaac tccaacatcc tttttcaaa gatgtaagtt gtcactgggc | 600 |
| acaacagcat taatcttgca aggtggttca ttgtttgggc tgtttcacct tggggtgatt | 660 |
| agaggtttat tgttacagga cctgatgcct aatattataa gtggtagctc tatgggggca | 720 |
| tgcgttgcaa gtttattcgg ttgcttgtcc aatgagcaac taaagcaatt attgaccgat | 780 |
| gacaacctct tgaatatcat caagaatgat gtagatttat taaaaagctg tggatacggt | 840 |
| aatttagagc agcacctaaa cctggggact ttgattcaga acctaataca ccacggttat | 900 |
| tctcaagacg tttatctttt tatccggttt gttatgaaat atattgttaa ggaaaaaact | 960 |
| tttgaagaag tttatcaaat tactggaaaa gttttcaata ttgttattca tccaactgat | 1020 |
| aaaatcatgc ctaatttact aaaattatgt gcaacccca acgtattaat caagtcagcc | 1080 |
| attgaatgtc cacttggttc tggtgtaatt tcagaggata catcactatt atgtaaaaat | 1140 |
| ttagaaaatg aaaattgagcc ttttcttaac atcaataaaa ataaacaagt caaatttctt | 1200 |
| acccccagaaa atgccaacaa tccgagcata acggagagcc cctatactag gttaacggaa | 1260 |
| ctattcaatg ttaataactt cattgttct ttggcgagac catacttggc accattggtg | 1320 |
| gtaaatgatt tgaagcatga aataaaaacg tcaaaatatt actattataa gcattatcca | 1380 |
| aatatgcctc ctaaaacgc gaatacagta agaaaaacac agagatcctc ttcgcaatca | 1440 |
| cccataaagg caggaactgt cgaggatctt gagccagagc ctttaatgag ccctgtgccc | 1500 |
| ccaagttcgg cagtcaacga ttcagcagag tacataatcc cagaattggg cataccgcag | 1560 |
| ttgaacttta ctgaaatgaa accgctggcg tttaaattta agtatcatct ggaaagaaaa | 1620 |
| ttaaaaaata ttgccactat ggaatttcga cataggatgg aggtattgga taatttaggc | 1680 |
| ctgttgtgct cattaataaa aagactaata attgatgaaa agactcccag atcagctacg | 1740 |
| gagattgctc tggtaccaag gatgaaaagt ctatcattaa caaggattat tgaaggtcaa | 1800 |
| ctaaacaaca ttccatactg gataaaatct ggtgaacgaa gtacatggcc cgcactagct | 1860 |
| ttaattaaga caagatgtgc agtcgaattt aaaattagacg acataataag agcaagacgg | 1920 |
| agtaggtag | 1929 |

| SEQ ID NO: 19 | moltype = DNA length = 2733 |
|---|---|
| FEATURE | Location/Qualifiers |
| source | 1..2733 |
| | mol_type = other DNA |
| | organism = synthetic construct |

SEQUENCE: 19

| | | |
|---|---|---|
| atgagcagca aaatatcaga tcttacatct acacaaaata gcccctcct tgttacgcaa | 60 |
| caactcatcg aaaatatatta cgaacagatc ctgggcactt cccagaacat aattcctatt | 120 |
| ttaaatccga gaacaagtt tattaggccc agtaaggata attcagatgt tgaaagggtg | 180 |
| gaggaggatg ctggtaaaag actgcaaact ggcaagaaca aaactacgaa caaggtaaat | 240 |
| ttcaacctgg atactggaaa cgaggataaa cttgacgatg accaagagac agtaacagaa | 300 |
| aatgaaaata tgatatcga gatggttgag acagacgaag aaggcaaggg | 360 |
| tcatctttag ccagtaaatg caatcattt ctttacaacg ttttttgtggg aaactatgaa | 420 |
| agagacattc ttattgacaa agtctgttca caaaagcaac atgcgatgtc atttgaagaa | 480 |
| tggtgttctg cgggcgccag attggatgac ctcactggga aaacagaatg gaagcagaaa | 540 |
| ttggaaagtc ccttgtatga ttacaagcta ataaagattt aacatctag aatgcgtgag | 600 |
| gagcgcttga ataggaatta cgctcaattg ttgtacatca ttaggacgaa ttgggtacga | 660 |

```
aacctgggaa atatgggaa  tgtaaacctg tataggcact ctcatgtagg caccaaatat  720
ttaattgacg agtatatgat ggagtctagg ttagcgctag aatctttaat ggagtctgat  780
cttgatgata gttacctttt gggtatactg caacaaacga gaagaaatat tggtcgtacc  840
gctttagttc tcagtggggg tggaactttt ggtcttttcc acatcggtgt ccttggtact  900
ctatttgaat tggatttatt acccagagtg attagtggta gcagtgctgt tgcaattgta  960
gccagcatat tatctgtcca tcacaaagaa gaaattccgg ttttactaaa tcatattttg 1020
gataaagaat tcaacatttt caaagacgat aaacagaaaa gtgaaagcga gaatttgtta 1080
ataaaaatat ctaggttctt caaaaacggt acgtggtttg ataacaagca tctggtaaat 1140
acaatgatag aattttttggg agatttgaca tttagggaag cttacaatag aacgggtaaa 1200
attttgaata taaccgtttc gccggcatct ttatttgaac aaccgcgctt gctgaataat 1260
ttgactgcac caaacgtcct gatttggtcc gccgtatgtg catcatgttc actaccggga 1320
attttcccct cgagcccact ttacgaaaaa gatccaaaaa cgggagaaag gaaaccatgg 1380
actggtagta gttcggtcaa atttgtcgat ggttctgtgg acaatgactt gcccatttct 1440
cgtcttttct gaaatgttcaa tgtggaccat attatcgcat gccaggtgaa ttcacgta 1500
tttccctttt tgaaactatc actatcctgt gttggcgggg aaattgagga cgaatttagt 1560
gcaagattaa agcaaaactt atcaagtata tacaattta tggccaatga agctattcat 1620
attctagaaa ttggaagtga gatgggaatt gccaaaaacg cgcttacaaa actgagatcg 1680
gtattatctc aacaatattc tggtgacatc actatttttgc ccgacatgtg tatgctttt  1740
agaataaagg agctgttgtc aaacccaaca aaagaatttt tattaaggga aatcaccaat 1800
ggtgcaaaag ctacgtggcc caaggtttcc attattcaaa atcactgtgg ccaggaattt 1860
gctctggata aggcgatttc ttatatcaaa ggtaggatga ttgtcacctc ctcttttaaaa 1920
accccttcc aatttgctga ttcagtcatt ggattaatta aagctccaga gcaaacgtca 1980
gatgagtcca aaaacccaga aaattcaaca ttgctaacta ggactccaac caagggtgac 2040
aatcatattt ccaatgtttt agatgacaac ttattagaat cagaatcgac aaactctttg 2100
ctattgttac gtgagaatgc aagcacatat gggcggtcac cttccgggtt tagaccgcgg 2160
tattccatta cgtccgcttc cctcaatccg cgtcaccaaa gaaggaaatc agatactatt 2220
tcaacttcaa ggcgaccagc caaatccttt tcattttcag ttgcttctcc cacatcaagg 2280
atgttgaggc aatccagcaa aatcaatgga cacccaccac caattctgca gaaaaaaaca 2340
agtatgggcc ggctaatgtt tcctatggat gccaagacct atgacccgga aagccatgaa 2400
cttatcccac attctgccag cattgaaaca cctgccatgg tagacaagaa attgcatttt 2460
ggccgaaaga gtagatactt gaggcatatg aacaaaaaat gggtcagcag tagcaacata 2520
ttatacacag attcggataa agaagaccat cctacattga gactgataag taacttcgat 2580
tcagacgcaa tgattcatag tgatttagcg ggcaatttca ggcgtcatag cattgatgga 2640
agaccccctt ctcaagctac aaagagctca ccgtttcgat cgaggccttc ttcttcaacg 2700
cagcacaaaa gcaccaccag ttttactcaa taa                              2733

SEQ ID NO: 20           moltype = DNA   length = 2250
FEATURE                 Location/Qualifiers
source                  1..2250
                        mol_type = other DNA
                        organism = synthetic construct
SEQUENCE: 20
atgtctaata ccttgccagt aacagaattt cttttatcca aatactacga actttccaac   60
actcctgcca cagactcatc atcgctcttc aaatggttat accacaagac tctctcccgt  120
aaacagctgc tcatatccga tttgtcttcc cagaaaaaac acgccatctc ctacgatcaa  180
tggaatgaca tagcgtcgcg attagacgac ttaacgggac tttccgaatg gaaaacaatc  240
gacgagtcct cgttgtataa ctataagctg ctgcaagact tgaccatccg tatgcgccat  300
ttgagaacca ctcacgacta ccatcgcctg ctttatctga ttagaactaa gtgggtccgt  360
aatcttggca acatgaataa cgttaatctt tacaggcact cgcataccgg cacaaaacaa  420
attatacatg actacctaga agagtctcaa gcagtgctca ccgcgctgat ccatcagtca  480
aatatgaacg atcactatct cctcggtatc ttgcaacaga cgagaagaaa catagggcga  540
acggctctcg tgcttagcgg tgggagcact ttcggccttt tccacattgg tgttcttgcc  600
gccctttttg aatcggacct gatgcctaag gtgatcagcg gtagcagtgc tggcgccatt  660
gttgccagca tatttttgcgt ccacacgacc caggaaattc cctccttgtt gaccaatgta  720
cttaatatgg agtttaacat cttcaatgac gacaattcaa aatctcccaa cgaaaactta  780
ctaatcaaga tatcgaggtt ctgccaaaac ggtacctggt tcaataatca acctttgatt  840
aacacaatgc tttcgttttt aggaaacttg acctttaggg aagcctacaa caagactgga  900
aaaatcctga atatcacagt ctcgcctgct tccatatacg aacagccgaa actactaaac  960
aatttaaccg ctccaaacgt tctcatctgg tctgccgtat gcgcttcttg ttctctacct 1020
ggagttttcc cctccacgcc gctattcgag aaagatcctc acactggaaa gattaaaag  1080
tgggggggcaa cgaatttaca tttatcaaac atgaaattca tggacggatc tgtagataat 1140
gacatgccca tttctcgtct ttctgaaatg ttcaatgtcg accacattat cgcctgccag 1200
gtaaatatac atgtctttcc cctgttaaag ttttcaaaca cttgcgttgg gggtgaaatt 1260
gaaaaggaaa ttaccgcccg tttcagaaac caagtaacga agatcttcaa atttttttcc 1320
gacgaaacta ttcattttt  agacatccta aaggagcttg agttccatcc ctatttgatg 1380
accaaattga aacacctttt tttacaacaa tactccggca atgtcacaat ttacccgat  1440
ctatcaatgg ttggtcaatt ccacgaagta ttgaagaacc cgtctcaact tttcctattg 1500
caccaaacca ctttaggtgc aagagctacc tggccgaaaa tttccatgat tcaaaataat 1560
tgtggccaag aattcgctct ggataaggcc atcacattcc taaggagaaa aataataatc 1620
tcttcgtcaa taaaaaaccc tttacaattc taccaacctc gattcagtga gcaaatcaaa 1680
tctctttcca taatggatgc tgacttgccg ggagttgact tggaagaatc ctcctccaat 1740
tcactatcaa ttatcaagtc tcccaacaaa acagcggcac cggaagatt  tcctcttcag 1800
ccattgcctt ctccatcttc taccttcaac aagaggaaaa tggatatgtt atcgccttct 1860
ccatcgccat ctacatctcc acaacgttca aaatcttcat tcacgcagca gggtacaagg 1920
cagaaggcaa attctttatc gtttgccatc ggtgcatcta gtttacggct aaagaaatca 1980
ccattgaagg ttccatcacg acctcaattc aaaaaaagat cttcttatta taatcaaaat 2040
atgtcggcag agatgaggaa aaatagaaaa aaatctggaa caatttcctc ttatgatgtt 2100
caaacaaact cggaagattt tcccataccg gctattgaaa acggttcatt tgataacact 2160
ttattcaatc caagcaggtt ccccatggac gctatgtcgc ctgccacaaa cgacaatttc 2220
```

```
atgaacaatt cagacatttt tcaaaattga                              2250

SEQ ID NO: 21           moltype = DNA   length = 311
FEATURE                 Location/Qualifiers
source                  1..311
                        mol_type = other DNA
                        organism = synthetic construct
SEQUENCE: 21
tctgttttga ctaaatggtt gggtttacca tctttcttgt tttctgtttt tgttttttat    60
tggtctttac caatctttgc tattttatat agaatcagat tcgcttcttt gggtaaaaga   120
aatgatatgt tggattgggc tagagctttg gttgcttatt ttagagttac tttgttgcaa   180
gctggtgaac atactttgta taaaggtggt ccatgtttgt atttgtgtaa tcatagatct   240
tgggctgatt ttttttattga tgcttatttg actgaaggta gagctgcttt aatgtctaga   300
tggttggtta t                                                        311

SEQ ID NO: 22           moltype = DNA   length = 33
FEATURE                 Location/Qualifiers
source                  1..33
                        mol_type = other DNA
                        organism = unidentified
SEQUENCE: 22
agtattatct ctgctggtcg gtacttaaat tgg                                33

SEQ ID NO: 23           moltype = DNA   length = 61
FEATURE                 Location/Qualifiers
source                  1..61
                        mol_type = other DNA
                        organism = unidentified
SEQUENCE: 23
aaaaaatcgg atgttgaatg ggcataaata taaatgtata tataagctat tacgccagct    60
g                                                                   61

SEQ ID NO: 24           moltype = DNA   length = 37
FEATURE                 Location/Qualifiers
source                  1..37
                        mol_type = other DNA
                        organism = unidentified
SEQUENCE: 24
tcatgacatt gacgagagtt tctctcgtac ccatatt                            37

SEQ ID NO: 25           moltype = DNA   length = 46
FEATURE                 Location/Qualifiers
source                  1..46
                        mol_type = other DNA
                        organism = unidentified
SEQUENCE: 25
tcaggggtaa ttaacttgtt aactttggag aagtaaatga aaaatg                  46

SEQ ID NO: 26           moltype = DNA   length = 66
FEATURE                 Location/Qualifiers
source                  1..66
                        mol_type = other DNA
                        organism = unidentified
SEQUENCE: 26
gaaagatggt aaacccaacc atttagtcaa aacagacata tagcttcaaa atgtttctac    60
tccttt                                                              66

SEQ ID NO: 27           moltype = DNA   length = 61
FEATURE                 Location/Qualifiers
source                  1..61
                        mol_type = other DNA
                        organism = unidentified
SEQUENCE: 27
cgaatacctc agaacatcat cttttcagca agtagttcta gaaaacttag attagattgc    60
t                                                                   61

SEQ ID NO: 28           moltype = DNA   length = 73
FEATURE                 Location/Qualifiers
source                  1..73
                        mol_type = other DNA
                        organism = unidentified
SEQUENCE: 28
cataaatata aatgtatata taagctatta cgccagctga attggagcga cctcatgcta    60
tactgagaaa gca                                                      73

SEQ ID NO: 29           moltype = DNA   length = 55
FEATURE                 Location/Qualifiers
source                  1..55
                        mol_type = other DNA
```

```
                                organism = unidentified
SEQUENCE: 29
cgaagatgtt gtggttagcg gccataattc ttcgccagag gtttggtcaa gtctc          55

SEQ ID NO: 30           moltype = DNA  length = 48
FEATURE                 Location/Qualifiers
source                  1..48
                        mol_type = other DNA
                        organism = unidentified
SEQUENCE: 30
tgcttgttgt gctgcttgtt ctgacaaaaa agatctcaaa acagaaga                  48

SEQ ID NO: 31           moltype = DNA  length = 68
FEATURE                 Location/Qualifiers
source                  1..68
                        mol_type = other DNA
                        organism = unidentified
SEQUENCE: 31
aaaggagtag aaacattttg aagctatatg tctgttttga ctaaatggtt gggtttacca     60
tctttctt                                                              68

SEQ ID NO: 32           moltype = DNA  length = 60
FEATURE                 Location/Qualifiers
source                  1..60
                        mol_type = other DNA
                        organism = unidentified
SEQUENCE: 32
gcaatctaat ctaagttttc tagaactact tgctgaaaag atgatgttct gaggtattcg     60

SEQ ID NO: 33           moltype = DNA  length = 74
FEATURE                 Location/Qualifiers
source                  1..74
                        mol_type = other DNA
                        organism = unidentified
SEQUENCE: 33
tgttttgtat gctatttcat ttttcattta cttctccaaa gttaacaagt taattacccc     60
tgaagccgcc ttgc                                                       74

SEQ ID NO: 34           moltype = DNA  length = 66
FEATURE                 Location/Qualifiers
source                  1..66
                        mol_type = other DNA
                        organism = unidentified
SEQUENCE: 34
aaccaacaaa ccaggaacat gagaagaacc caaagtcata tagcttcaaa atgtttctac     60
tccttt                                                                66

SEQ ID NO: 35           moltype = DNA  length = 66
FEATURE                 Location/Qualifiers
source                  1..66
                        mol_type = other DNA
                        organism = unidentified
SEQUENCE: 35
aaaggagtag aaacattttg aagctatatg actttgggtt cttctcatgt tcctggtttg     60
ttggtt                                                                66

SEQ ID NO: 36           moltype = DNA  length = 54
FEATURE                 Location/Qualifiers
source                  1..54
                        mol_type = other DNA
                        organism = unidentified
SEQUENCE: 36
ttgaccaaac ctctggcgaa gaattatggc cgctaaccac aacatcttcg ccgc           54

SEQ ID NO: 37           moltype = DNA  length = 51
FEATURE                 Location/Qualifiers
source                  1..51
                        mol_type = other DNA
                        organism = unidentified
SEQUENCE: 37
tcttctgttt tgagatcttt tttgtcagaa caagcagcac aacaagcagt t              51

SEQ ID NO: 38           moltype = DNA  length = 59
FEATURE                 Location/Qualifiers
source                  1..59
                        mol_type = other DNA
                        organism = unidentified
SEQUENCE: 38
aaaccaggaa catgagaaga acccaaagta tggccgctaa ccacaacatc ttcgccgct      59
```

```
SEQ ID NO: 39          moltype = DNA  length = 65
FEATURE                Location/Qualifiers
source                 1..65
                       mol_type = other DNA
                       organism = unidentified
SEQUENCE: 39
aaaggagtag aaacattttg aagctatatg tcagaacaag cagcacaaca agcagttaat    60
aatgc                                                                65

SEQ ID NO: 40          moltype = DNA  length = 38
FEATURE                Location/Qualifiers
source                 1..38
                       mol_type = other DNA
                       organism = unidentified
SEQUENCE: 40
ttaccttcat atgacaaaat ttcgttggac tcatcgtc                            38

SEQ ID NO: 41          moltype = DNA  length = 60
FEATURE                Location/Qualifiers
source                 1..60
                       mol_type = other DNA
                       organism = unidentified
SEQUENCE: 41
tacctcagaa catcatcttt tcagcaagta ttttttgct cgaattcact gacggaggga    60

SEQ ID NO: 42          moltype = DNA  length = 50
FEATURE                Location/Qualifiers
source                 1..50
                       mol_type = other DNA
                       organism = unidentified
SEQUENCE: 42
gcttcagggg taattaactt gttaacttca catttttaga gtagtatata              50

SEQ ID NO: 43          moltype = DNA  length = 39
FEATURE                Location/Qualifiers
source                 1..39
                       mol_type = other DNA
                       organism = unidentified
SEQUENCE: 43
ctttagcaat atcggacaaa cagccgtatt ttttattct                          39

SEQ ID NO: 44          moltype = DNA  length = 39
FEATURE                Location/Qualifiers
source                 1..39
                       mol_type = other DNA
                       organism = unidentified
SEQUENCE: 44
ctatcttggg ggtacgaaac ttagcaatat atttagcaa                          39

SEQ ID NO: 45          moltype = DNA  length = 51
FEATURE                Location/Qualifiers
source                 1..51
                       mol_type = other DNA
                       organism = unidentified
SEQUENCE: 45
tggaccagaa ctacctgtga aattaatgtt ggaagcgatc agcagcagaa t            51

SEQ ID NO: 46          moltype = DNA  length = 48
FEATURE                Location/Qualifiers
source                 1..48
                       mol_type = other DNA
                       organism = unidentified
SEQUENCE: 46
ctaacaaaat agcaaatttc gtcaaaaaat ggccaaaaac gacagatg                48

SEQ ID NO: 47          moltype = DNA  length = 40
FEATURE                Location/Qualifiers
source                 1..40
                       mol_type = other DNA
                       organism = unidentified
SEQUENCE: 47
gtgaagacaa attatctaag gtccaactct acgaagattt                         40

SEQ ID NO: 48          moltype = DNA  length = 38
FEATURE                Location/Qualifiers
source                 1..38
                       mol_type = other DNA
                       organism = unidentified
```

```
SEQUENCE: 48
atagacgttt ctaaacccaa atgaatccaa gttgccga                                    38

SEQ ID NO: 49          moltype = DNA  length = 64
FEATURE                Location/Qualifiers
source                 1..64
                       mol_type = other DNA
                       organism = unidentified
SEQUENCE: 49
tcaatgacga ggttctcacc cctgcccagg tatcttgtat tttgtcacct cgtaggagct            60
actt                                                                        64

SEQ ID NO: 50          moltype = DNA  length = 45
FEATURE                Location/Qualifiers
source                 1..45
                       mol_type = other DNA
                       organism = unidentified
SEQUENCE: 50
tcctagcgct caccaagctc tgaaatactt atgaaggcat gcatg                            45

SEQ ID NO: 51          moltype = DNA  length = 42
FEATURE                Location/Qualifiers
source                 1..42
                       mol_type = other DNA
                       organism = unidentified
SEQUENCE: 51
aggatcattc tggtaatacc ccatttaaaa tacctcatcg aa                               42

SEQ ID NO: 52          moltype = DNA  length = 63
FEATURE                Location/Qualifiers
source                 1..63
                       mol_type = other DNA
                       organism = unidentified
SEQUENCE: 52
gtttccctcc gtcagtgaat tcgagcaaaa aaatacttgc tgaaaagatg atgttctgag            60
gta                                                                         63

SEQ ID NO: 53          moltype = DNA  length = 50
FEATURE                Location/Qualifiers
source                 1..50
                       mol_type = other DNA
                       organism = unidentified
SEQUENCE: 53
tatatactac tctaaaaatg tgaagttaac aagttaatta ccctgaagc                        50

SEQ ID NO: 54          moltype = DNA  length = 51
FEATURE                Location/Qualifiers
source                 1..51
                       mol_type = other DNA
                       organism = unidentified
SEQUENCE: 54
ttctgctgct gatcgcttcc aacattaatt tcacaggtag ttctggtcca t                     51

SEQ ID NO: 55          moltype = DNA  length = 46
FEATURE                Location/Qualifiers
source                 1..46
                       mol_type = other DNA
                       organism = unidentified
SEQUENCE: 55
atctgtcgtt tttggccatt ttttgacgaa atttgctatt ttgtta                           46

SEQ ID NO: 56          moltype = DNA  length = 48
FEATURE                Location/Qualifiers
source                 1..48
                       mol_type = other DNA
                       organism = unidentified
SEQUENCE: 56
catgcatgcc ttcataagta tttcagagct tggtgagcgc taggagtc                         48

SEQ ID NO: 57          moltype = DNA  length = 55
FEATURE                Location/Qualifiers
source                 1..55
                       mol_type = other DNA
                       organism = unidentified
SEQUENCE: 57
ctacgaggtg acaaaataca agatacctgg gcaggggtga gaacctcgtc attga                 55

SEQ ID NO: 58          moltype = DNA  length = 42
FEATURE                Location/Qualifiers
```

```
                        -continued source                  1..42
                        mol_type = other DNA
                        organism = unidentified
SEQUENCE: 58
atagcctcga cgccagcttt gattagttca tccgggttcc cg                       42

SEQ ID NO: 59           moltype = DNA   length = 69
FEATURE                 Location/Qualifiers
source                  1..69
                        mol_type = other DNA
                        organism = unidentified
SEQUENCE: 59
cttcaggggt aattaacttg ttaactttat cgtttccact tttttctgtc ttattttttt    60
tattgatag                                                            69

SEQ ID NO: 60           moltype = DNA   length = 72
FEATURE                 Location/Qualifiers
source                  1..72
                        mol_type = other DNA
                        organism = unidentified
SEQUENCE: 60
acatctttga gttgccgtta agccttgctg aaaagatgat gttctgaggt attcgtatcg    60
ctagcttgat ac                                                        72

SEQ ID NO: 61           moltype = DNA   length = 54
FEATURE                 Location/Qualifiers
source                  1..54
                        mol_type = other DNA
                        organism = unidentified
SEQUENCE: 61
atacctcaga acatcatctt ttcagcaagg cttaacggca actcaaagat gtga          54

SEQ ID NO: 62           moltype = DNA   length = 42
FEATURE                 Location/Qualifiers
source                  1..42
                        mol_type = other DNA
                        organism = unidentified
SEQUENCE: 62
ttggtcctat tcagcgacca atcagtgctt cctgcccact tt                       42

SEQ ID NO: 63           moltype = DNA   length = 55
FEATURE                 Location/Qualifiers
source                  1..55
                        mol_type = other DNA
                        organism = unidentified
SEQUENCE: 63
aaaagtggaa acgataaagt taacaagtta attacccctg aagccgcctt gcatg         55

SEQ ID NO: 64           moltype = DNA   length = 37
FEATURE                 Location/Qualifiers
source                  1..37
                        mol_type = other DNA
                        organism = unidentified
SEQUENCE: 64
gggatcctct tgcgaagcac gctcgctggg cctggaa                             37

SEQ ID NO: 65           moltype = DNA   length = 64
FEATURE                 Location/Qualifiers
source                  1..64
                        mol_type = other DNA
                        organism = unidentified
SEQUENCE: 65
acaaatagc aaatttcgtc aaaaagaaaa cacgggcttg cttatatatc ctctagatat     60
tctt                                                                 64

SEQ ID NO: 66           moltype = DNA   length = 77
FEATURE                 Location/Qualifiers
source                  1..77
                        mol_type = other DNA
                        organism = unidentified
SEQUENCE: 66
gagtacaggt atatgtaata aaagtctgaa ttaatttcac aggtagttct ggtccattgg    60
tgaaagtttg cggcttg                                                   77

SEQ ID NO: 67           moltype = DNA   length = 62
FEATURE                 Location/Qualifiers
source                  1..62
                        mol_type = other DNA
                        organism = unidentified
```

```
SEQUENCE: 67
gaactacctg tgaaattaat tcagactttt attacatata cctgtactcc cttcaataat    60
ta                                                                  62

SEQ ID NO: 68           moltype = DNA   length = 45
FEATURE                 Location/Qualifiers
source                  1..45
                        mol_type = other DNA
                        organism = unidentified
SEQUENCE: 68
gttattatgt tggcaatgga aaagttgcgt accgagatac cgtaa                    45

SEQ ID NO: 69           moltype = DNA   length = 62
FEATURE                 Location/Qualifiers
source                  1..62
                        mol_type = other DNA
                        organism = unidentified
SEQUENCE: 69
atataagcaa gcccgtgttt tcttttttgac gaaatttgct attttgttag agtcttttac   60
ac                                                                  62

SEQ ID NO: 70           moltype = DNA   length = 36
FEATURE                 Location/Qualifiers
source                  1..36
                        mol_type = other DNA
                        organism = unidentified
SEQUENCE: 70
tgctggagca agctccgtct ccagctcggg aagtgt                              36

SEQ ID NO: 71           moltype = DNA   length = 66
FEATURE                 Location/Qualifiers
source                  1..66
                        mol_type = other DNA
                        organism = unidentified
SEQUENCE: 71
cgaggttctc acccctgccc aggtattgaa caattcagac attttcaaa attgaaatga    60
aagaca                                                              66

SEQ ID NO: 72           moltype = DNA   length = 69
FEATURE                 Location/Qualifiers
source                  1..69
                        mol_type = other DNA
                        organism = unidentified
SEQUENCE: 72
acaaggaaga cggttctgtt tcgttgctag agcttggtga gcgctaggag tcactgccag   60
gtatcgttt                                                           69

SEQ ID NO: 73           moltype = DNA   length = 61
FEATURE                 Location/Qualifiers
source                  1..61
                        mol_type = other DNA
                        organism = unidentified
SEQUENCE: 73
cctagcgctc accaagctct agcaacgaaa cagaaccgtc ttccttgtgc tgtttatgat   60
g                                                                   61

SEQ ID NO: 74           moltype = DNA   length = 54
FEATURE                 Location/Qualifiers
source                  1..54
                        mol_type = other DNA
                        organism = unidentified
SEQUENCE: 74
atttcctatg aataatcaag acataatgaa ttttcaatgg ctattgaact tccc          54

SEQ ID NO: 75           moltype = DNA   length = 69
FEATURE                 Location/Qualifiers
source                  1..69
                        mol_type = other DNA
                        organism = unidentified
SEQUENCE: 75
aattttgaaa atgtctgaa ttgttcaata cctgggcagg ggtgagaacc tcgtcattga   60
tggacaggt                                                           69
```